United States Patent
Bogaert et al.

(10) Patent No.: US 10,552,771 B2
(45) Date of Patent: Feb. 4, 2020

(54) ANALYZING DATA MANAGEMENT-RELATED AND/OR CONTRACT MANAGEMENT-RELATED OPERATIONS OF AN ORGANIZATION

(71) Applicant: Accenture Global Solutions Limited, Dublin (IE)

(72) Inventors: Marjorie P. Bogaert, Clayton, CA (US); Doreen Colburn, Millbrook, AL (US); John M. Froehlich, Benicia, CA (US); Betty J. Gillespie, Grand Island, NY (US); Kelsey Marie Ghon, San Francisco, CA (US); Arindam Guha, Wethersfield, CA (US); Daniel Huedig, Schweich (DE); Margaret Hughes, South San Francisco, CA (US); Amit Jindal, Palo Alto, CA (US); Franklin C. Lee, San Francisco, CA (US); Jennifer Nichol, Lakeland, FL (US); Frank Pino, Cream Ridge, NJ (US); Cristi Velastegui, Kitty Hawk, NC (US); Barbara Slagg, Ramsey, NJ (US)

(73) Assignee: Accenture Global Solutions Limited, Dublin (IE)

( * ) Notice: Subject to any disclaimer, the term of this patent is extended or adjusted under 35 U.S.C. 154(b) by 0 days.

(21) Appl. No.: 15/689,661

(22) Filed: Aug. 29, 2017

(65) Prior Publication Data
US 2018/0357587 A1 Dec. 13, 2018

Related U.S. Application Data

(60) Provisional application No. 62/517,622, filed on Jun. 9, 2017.

(51) Int. Cl.
*G06Q 10/06* (2012.01)

(52) U.S. Cl.
CPC ....... *G06Q 10/0631* (2013.01); *G06Q 10/067* (2013.01); *G06Q 10/06395* (2013.01)

(58) Field of Classification Search
CPC ......... G06Q 10/0631; G06Q 10/06395; G06Q 10/067
(Continued)

(56) References Cited

U.S. PATENT DOCUMENTS

| 2012/0204103 A1* | 8/2012 | Stevens ................. G06Q 10/10 715/273 |
| 2016/0366299 A1* | 12/2016 | Sato .................. H04N 1/32427 |
| 2017/0061558 A1* | 3/2017 | Kogut-O'Connell ....................... G06Q 50/18 |

OTHER PUBLICATIONS

Mokotedi, Aubrey Pheto, A Framework for Web-Based Collaborative Environments, (Year: 2007).*
(Continued)

*Primary Examiner* — Charles Guiliano
(74) *Attorney, Agent, or Firm* — Harrity & Harrity, LLP

(57) ABSTRACT

A device may receive first data that identifies operations of an organization. The operations may be associated with a first manner in which the organization stores second data or a second manner in which the organization generates a contract. The device may process the first data to identify the operations of the organization. The device may perform a first analysis of the first data to determine whether the operations of the organization satisfy a set of rules. The set of rules may indicate the first manner in which the organization is to store the second data. The device may perform a second analysis of the second data to identify an error associated with the second data. The device may perform an action to modify the operations of the organization or to facilitate fixing of the error based on a result of the first analysis or the second analysis.

20 Claims, 14 Drawing Sheets

(58) Field of Classification Search
USPC .............................................. 705/7.12, 7.41
See application file for complete search history.

(56) References Cited

OTHER PUBLICATIONS

Wikipedia, "Contract management," http://en.wikipedia.org/wiki/Contract_management, Aug. 17, 2017, 4 pages.
Wikipedia, "Data management," http://en.wikipedia.org/wiki/Data_management, Aug. 22, 2017, 5 pages.

* cited by examiner

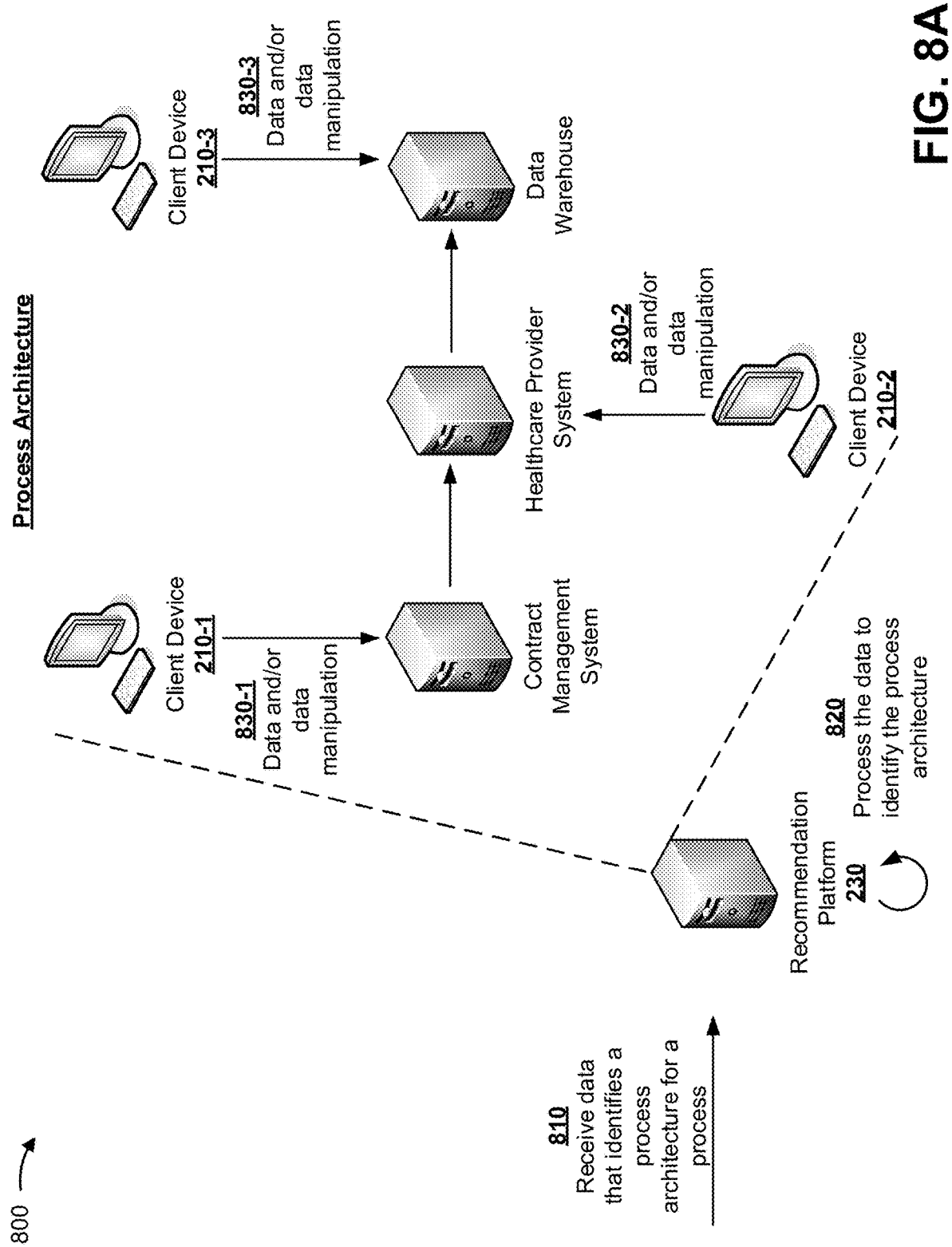

ANALYZING DATA MANAGEMENT-RELATED AND/OR CONTRACT MANAGEMENT-RELATED OPERATIONS OF AN ORGANIZATION

RELATED APPLICATION(S)

This application claims priority under 35 U.S.C. § 119 to U.S. Provisional Patent Application No. 62/517,622, filed on Jun. 9, 2017, the content of which is incorporated by reference herein in its entirety.

BACKGROUND

Data management may include the development, execution and supervision of plans, policies, programs, and practices that control, protect, deliver, and enhance the value of data and information assets. Integrated data management is a tools approach to facilitate data management and improve performance. Integrated data management consists of an integrated, modular environment to manage enterprise application data, and optimize data-driven applications over the lifetime of the data. Contract management (or contract administration) may include the management of contracts made with customers, vendors, partners, or employees. Contract management may include negotiating terms and/or conditions in contracts and ensuring compliance with the terms and/or conditions.

SUMMARY

According to some possible implementations, a device may include one or more processors to receive first data that identifies operations of an organization. The first data may be received from an external information source. The operations may be associated with a first manner in which the organization stores second data or a second manner in which the organization generates a contract. The device may process the first data to identify the operations of the organization. The device may perform a first analysis of the first data to determine whether the operations of the organization satisfy a set of rules. The set of rules may indicate the first manner in which the organization is to store the second data. The device may perform a second analysis of the second data to identify an error associated with the second data after performing the first analysis. The device may perform an action to modify the operations of the organization or to facilitate fixing of the error based on a result of the first analysis or the second analysis.

According to some possible implementations, a method may include receiving, by a device, first data that identifies operations of an organization. The first data may identify at least one of a process architecture of a process of the organization, a set of permissions related to manipulating second data stored in a system associated with the organization, a set of points in the process where the second data can be manipulated, or a set of quality control procedures related to the second data. The method may include processing, by the device, the first data to identify the operations of the organization. The method may include performing, by the device, a first analysis of the first data to determine whether the operations of the organization satisfy a set of rules based on processing the first data. The set of rules may be determined from at least one of an organization operating model, text data, or audio data. The method may include performing, by the device, a second analysis of the second data to determine whether the second data satisfies the set of rules after performing the first analysis. The method may include performing, by the device, an action to modify the operations of the organization or the second data based on a result of the first analysis or the second analysis.

According to some possible implementations, a non-transitory computer-readable medium may store one or more instructions that, when executed by one or more processors, cause the one or more processors to receive, from one or more devices, first data that identifies one or more operations of one or more organizations. The one or more operations may relate to management of second data. The one or more instructions, when executed by the one or more processors, may cause the one or more processors to process the first data to identify the one or more operations of the one or more organizations using one or more processing techniques. The one or more processing techniques may include at least one of natural language processing, or speech-to-text processing. The one or more instructions, when executed by the one or more processors, may cause the one or more processors to perform one or more first analyses of the first data based on processing the first data using the one or more techniques. The one or more first analyses may be used to identify one or more deficiencies related to the one or more operations of the one or more organizations. The one or more instructions, when executed by the one or more processors, may cause the one or more processors to perform one or more second analyses of the second data after performing the one or more first analyses. The one or more second analyses may be used to identify one or more deficiencies related to the second data. The one or more instructions, when executed by the one or more processors, may cause the one or more processors to perform one or more actions to modify the one or more operations of the one or more organizations or to modify the second data based on one or more results of the one or more first analyses or the one or more second analyses. The one or more actions may positively impact the one or more operations or the second data.

BRIEF DESCRIPTION OF THE DRAWINGS

FIGS. 8A and 8B are diagrams of an example implementation relating to the example process shown in FIG. 4.

DETAILED DESCRIPTION

The following detailed description of example implementations refers to the accompanying drawings. The same reference numbers in different drawings may identify the same or similar elements.

An organization may implement a process with respect to data stored across various systems. Additionally, or alternatively, the organization may implement a process with respect to negotiating, generating, and/or monitoring a contract and/or contract-related data. The organization may lack a technique for efficiently and accurately performing a computer-based analysis of the operations of the organization and/or to improve the manner in which the organization operates, particularly with respect to the data stored across the various systems and/or contract management.

Implementations, described herein, provide a recommendation platform that is capable of processing data to determine a manner in which an organization operates, particularly with respect to data management techniques and/or contract management, determining whether the operations of the organization satisfy a set of rules, and/or performing an action to modify the operations of the organization to improve the operations. In this way, implementations described herein increase an efficiency of the operations, thereby conserving processing resources of a device used to implement the operations. In addition, implementations described herein reduce errors related to the operations, thereby conserving processing resources, of a device used to implement the operations, that would otherwise be consumed due to error-prone operations.

Figure 1A:
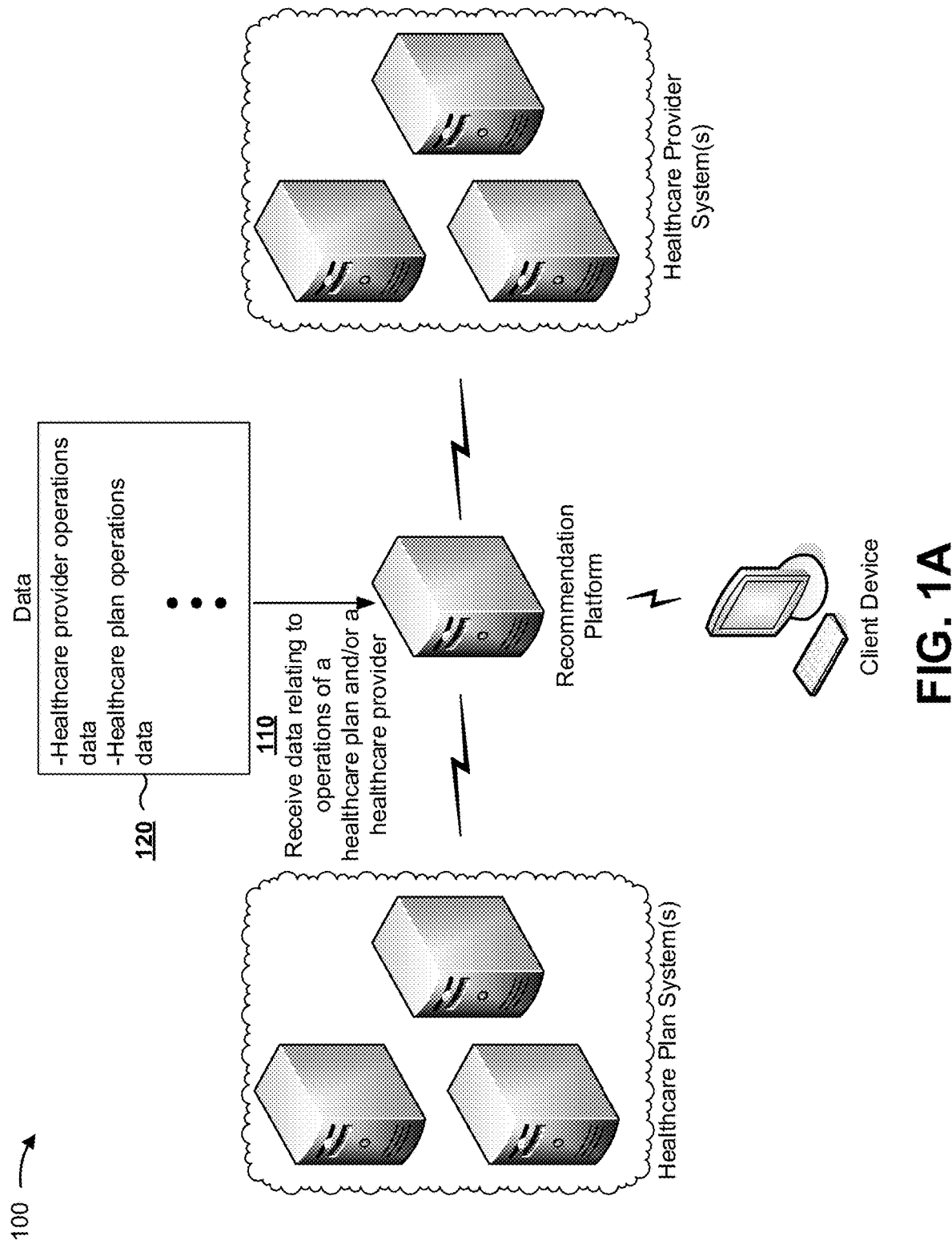
FIGS. 1A-1C are diagrams of an overview of an example implementation described herein.
Figure 1B:
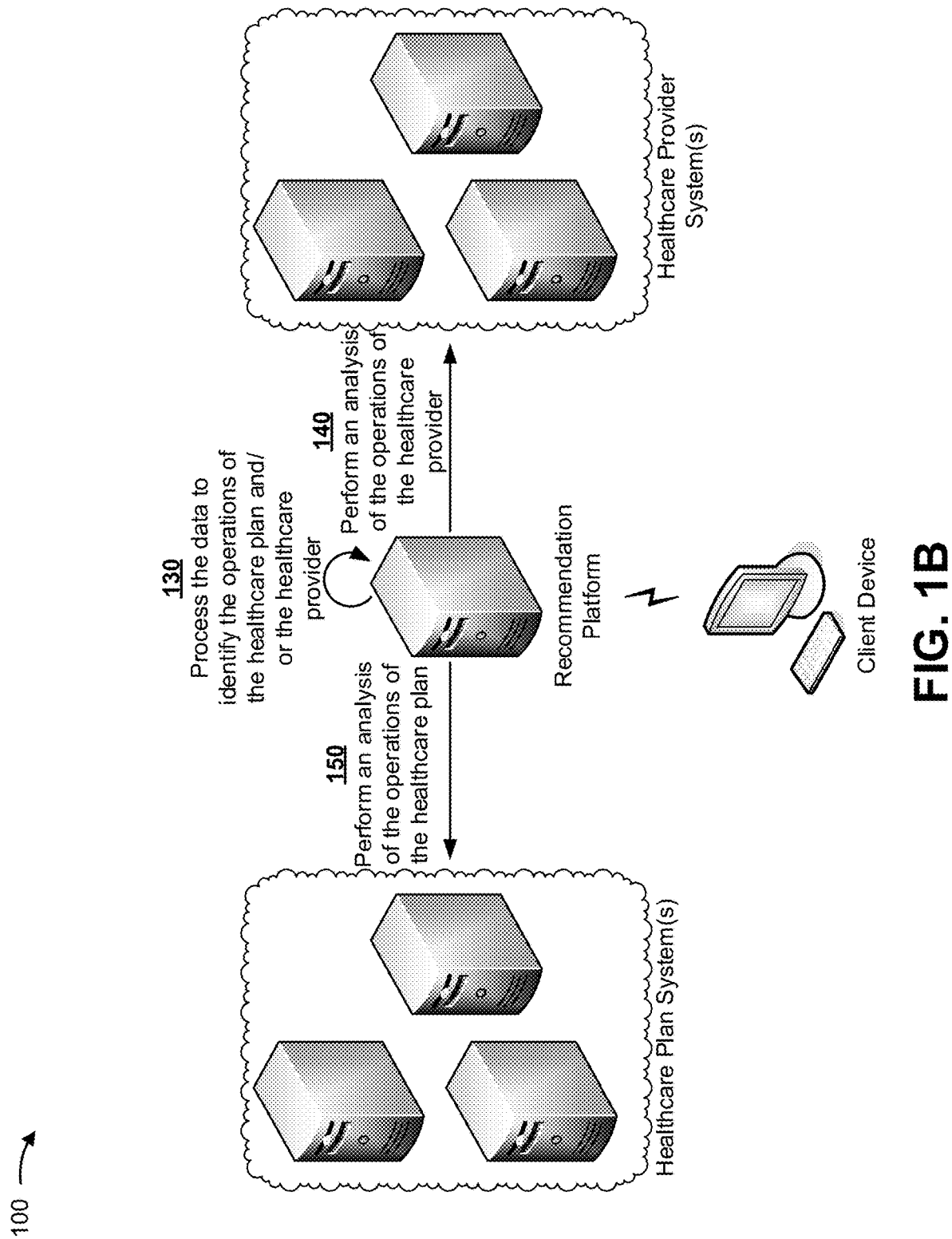
Figure 1C:
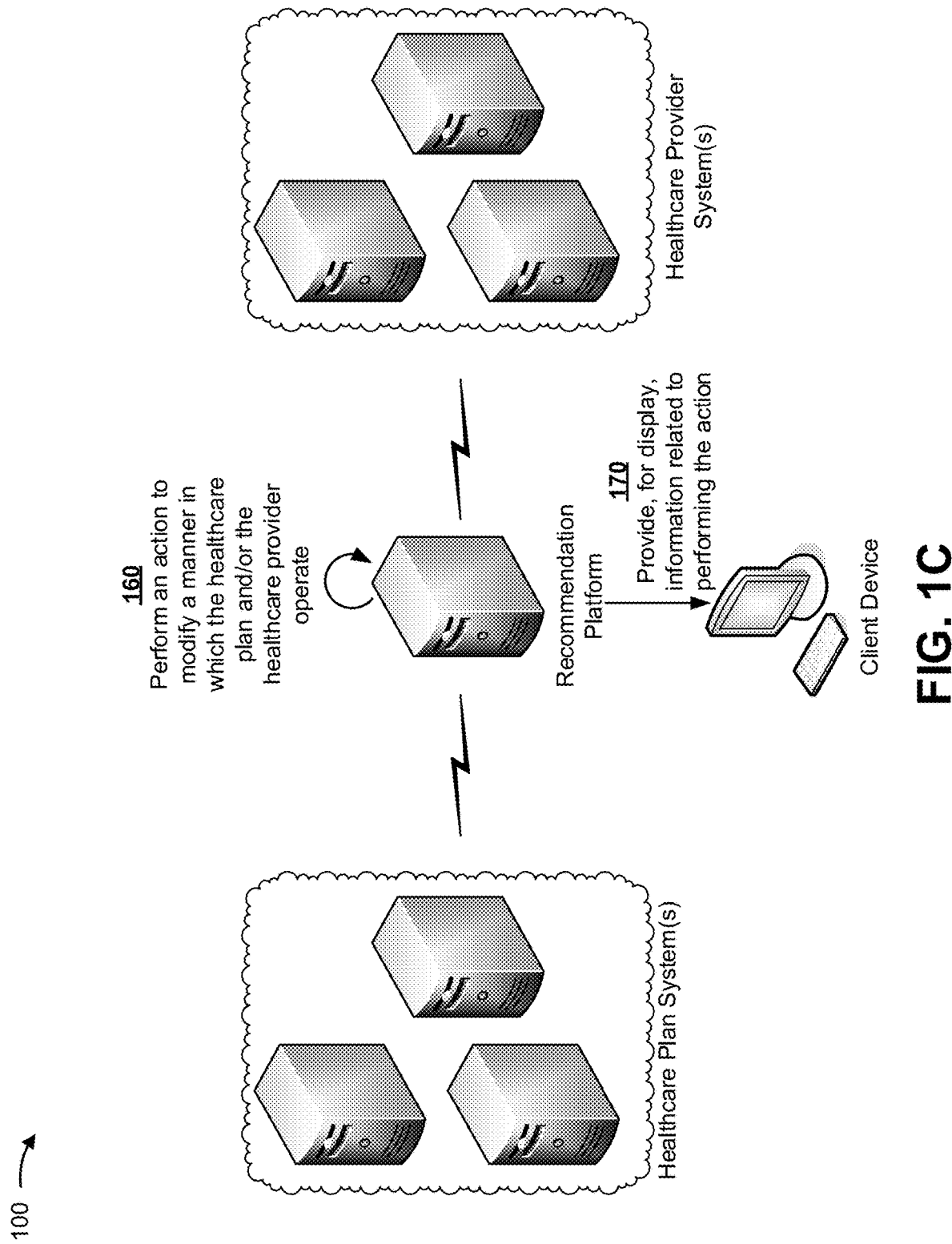

FIGS. 1A-1C are diagrams of an overview of an example implementation 100 described herein. As shown in FIGS. 1A-1C, example implementation 100 will be described in the context of healthcare plan system(s), healthcare provider system(s), a client device, and a recommendation platform. In other contexts, different systems and/or devices may be used.

As shown in FIG. 1A, and as shown by reference number 110, the recommendation platform may receive data relating to operations of a healthcare plan and/or a healthcare provider. For example, the recommendation platform may receive the data from the healthcare plan system(s) and/or the healthcare provider system(s).

Reference number 120 shows an example of the type of data that the recommendation platform may receive (e.g., healthcare provider operations data and/or healthcare plan operations data). In some implementations, the operations may include a manner in which the healthcare plan and/or healthcare provider contract, controls related to data stored in the healthcare plan system(s) and/or the healthcare provider system(s), consistency of data stored in the healthcare plan system(s) and/or the healthcare provider system(s), and/or the like. In some implementations, the recommendation platform may receive millions, billions, trillions, etc. of data elements when receiving the data. In this way, the recommendation platform receives a data set that cannot be received manually or processed objectively by a human actor.

As shown in FIG. 1B, and as shown by reference number 130, the recommendation platform may process the data to identify the operations of the healthcare plan and/or the healthcare provider. For example, the recommendation platform may use natural language processing, machine learning, artificial intelligence, and/or the like to identify the operations (e.g., a manner in which the healthcare plan and/or the healthcare provider contract, how and when data stored in systems associated with the healthcare plan and/or the healthcare provider can be manipulated, consistency of data between systems of the healthcare plan and the healthcare provider, etc.).

As shown by reference numbers 140 and 150, the recommendation platform may perform an analysis of the operations of the healthcare provider and/or healthcare plan. For example, the recommendation platform may verify that the manner in which the data is stored satisfies a set of rules. Additionally, or alternatively, and as another example, the recommendation platform may determine whether the manner in which the healthcare plan and/or the healthcare provider form a contract satisfies a set of rules. Additionally, or alternatively, and as another example, the recommendation platform may determine whether data is properly managed (e.g., according to the set of rules), such as to determine whether the organization has controls that enforce proper management of the data. Additionally, or alternatively, and as another example, the recommendation platform may determine whether data in the healthcare provider system(s) matches data stored in the healthcare plan system(s), such as to determine whether a healthcare plan and/or a healthcare provider have implemented a data management technique to ensure consistent data across systems. In this way, the recommendation platform may identify a deficiency related to the operations of the healthcare plan and/or the healthcare provider.

As shown in FIG. 1C, and as shown by reference number 160, the recommendation platform may perform an action (e.g., to modify a manner in which the healthcare plan and/or the healthcare provider operate). In some implementations, for example, the recommendation platform may adjust a setting of the healthcare plan system(s) and/or the healthcare provider system(s) to restrict manipulation of data. Additionally, or alternatively, and as another example, the recommendation platform may retrieve data from a first system and provide the data to a second system to improve data consistency among the first and second systems. Additionally, or alternatively, and as another example, the recommendation platform may identify rules related to data management that are not satisfied. Additionally, or alternatively, and as another example, the recommendation platform may determine whether contract management-related operations of the organization satisfy a set of rules. As shown by reference number 170, the recommendation platform may provide, for display, information related to performing the action to a client device.

In this way, some implementations described herein increase an efficiency of operations of an organization, particularly operations related to data management and/or contract management, thereby conserving processing resources of a device used to implement the operations. In addition, some implementations described herein reduce errors related to the operations, thereby conserving processing resources, of a device used to implement the operations, that would otherwise be used to implement the operations.

As indicated above, FIGS. 1A-1C are provided merely as an example. Other examples are possible and may differ from what was described with regard to FIGS. 1A-1C. Although implementations are described in the context of healthcare organizations (e.g., a healthcare plan and a healthcare provider), these implementations equally apply to other kinds of organizations, such as organizations relating to manufacturing, construction, information technology, and/or the like.

Figure 2:
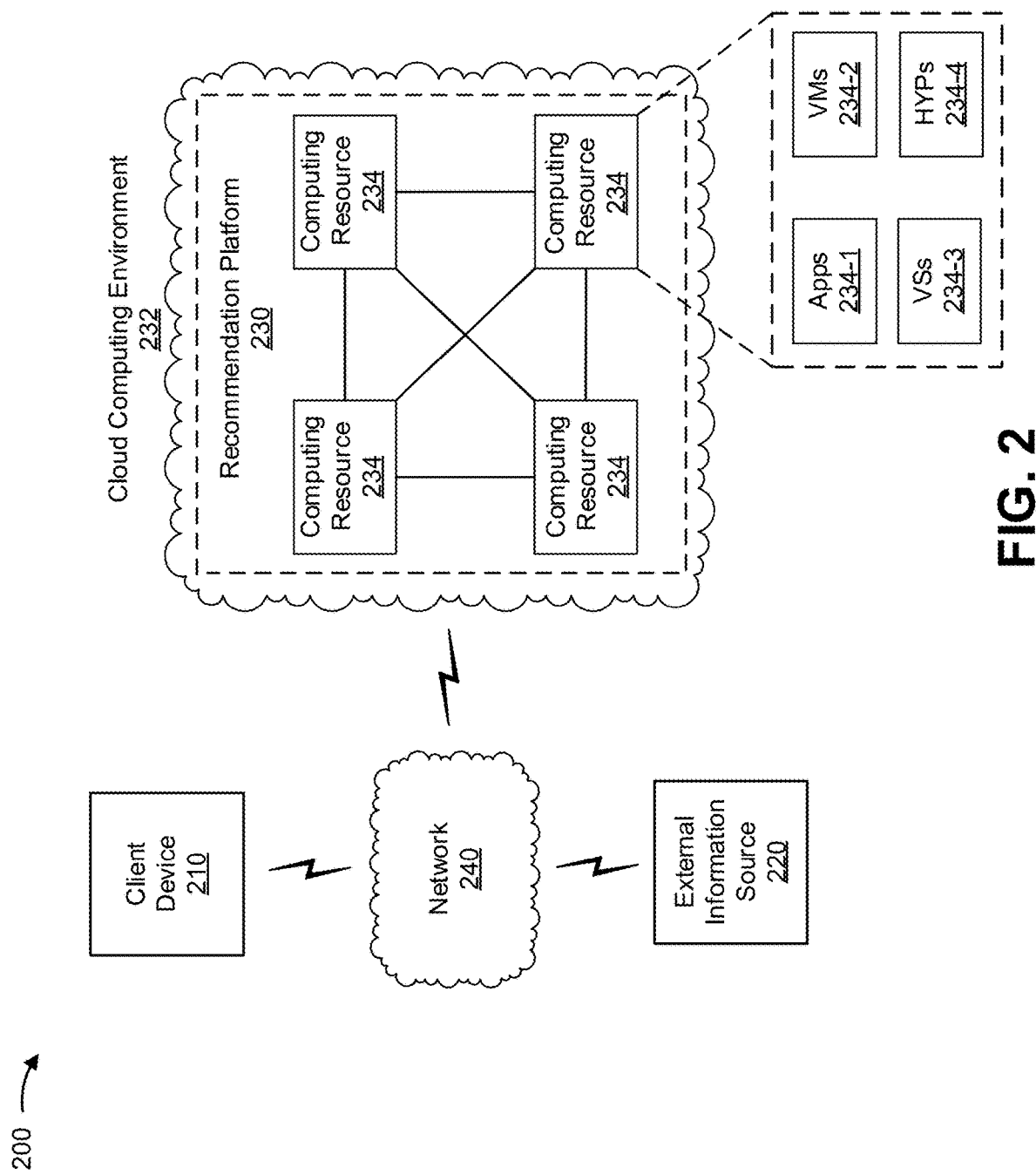
FIG. 2 is a diagram of an example environment in which systems and/or methods, described herein, may be implemented.

FIG. 2 is a diagram of an example environment 200 in which systems and/or methods, described herein, may be implemented. As shown in FIG. 2, environment 200 may include client device 210, external information source 220, recommendation platform 230, cloud computing environment 232, and a set of computing resources 234. Devices of environment 200 may interconnect via wired connections, wireless connections, or a combination of wired and wireless connections.

Client device 210 includes one or more devices capable of receiving, generating, storing, processing, and/or providing information associated with analyzing operations of an organization related to data management and/or contract management. For example, client device 210 may include a desktop computer, a mobile phone (e.g., a smart phone or a radiotelephone), a laptop computer, a tablet computer, a gaming device, a wearable communication device (e.g., a smart wristwatch or a pair of smart eyeglasses), or a similar type of device. In some implementations, client device 210 may receive data associated with an analysis that recommendation platform 230 has performed, as described elsewhere herein. Additionally, or alternatively, client device 210 may provide information for display (e.g., information related to an analysis that recommendation platform 230 has performed), as described elsewhere herein.

External information source 220 includes one or more devices capable of receiving, generating, storing, processing, and/or providing information associated with analyzing operations of an organization related to data management and/or contract management. For example, external information source 220 may include a server (e.g., in a data center or a cloud computing environment), a data center (e.g., a multi-server micro data center), a workstation computer, a virtual machine (VM) provided in a cloud computing environment, a system that an organization uses to implement a process and/or operations of the organization, or a similar type of device. In some implementations, external information source 220 may provide, to recommendation platform 230, information related to data management and/or contract management operations of an organization, as described elsewhere herein. Additionally, or alternatively, external information source 220 may store information related to an analysis of data management and/or contract management operations of an organization, as described elsewhere herein.

Recommendation platform 230 includes one or more devices capable of analyzing data related to data management and/or contract management operations of an organization. For example, recommendation platform 230 may include a cloud server or a group of cloud servers. In some implementations, recommendation platform 230 may be designed to be modular such that certain software components can be swapped in or out depending on a particular need. As such, recommendation platform 230 may be easily and/or quickly reconfigured for different uses.

In some implementations, as shown, recommendation platform 230 may be hosted in cloud computing environment 232. Notably, while implementations described herein describe recommendation platform 230 as being hosted in cloud computing environment 232, in some implementations, recommendation platform 230 may not be cloud-based (i.e., may be implemented outside of a cloud computing environment) or may be partially cloud-based.

Cloud computing environment 232 includes an environment that hosts recommendation platform 230. Cloud computing environment 232 may provide computation, software, data access, storage, and/or other services that do not require end-user knowledge of a physical location and configuration of a system and/or a device that hosts recommendation platform 230. As shown, cloud computing environment 232 may include a group of computing resources 234 (referred to collectively as "computing resources 234" and individually as "computing resource 234").

Computing resource 234 includes one or more personal computers, workstation computers, server devices, or another type of computation and/or communication device. In some implementations, computing resource 234 may host recommendation platform 230. The cloud resources may include compute instances executing in computing resource 234, storage devices provided in computing resource 234, data transfer devices provided by computing resource 234, etc. In some implementations, computing resource 234 may communicate with other computing resources 234 via wired connections, wireless connections, or a combination of wired and wireless connections.

As further shown in FIG. 2, computing resource 234 may include a group of cloud resources, such as one or more applications ("APPs") 234-1, one or more virtual machines ("VMs") 234-2, one or more virtualized storages ("VSs") 234-3, or one or more hypervisors ("HYPs") 234-4.

Application 234-1 includes one or more software applications that may be provided to or accessed by one or more devices of environment 200. Application 234-1 may eliminate a need to install and execute the software applications on devices of environment 200. For example, application 234-1 may include software associated with recommendation platform 230 and/or any other software capable of being provided via cloud computing environment 232. In some implementations, one application 234-1 may send/receive information to/from one or more other applications 234-1, via virtual machine 234-2.

Virtual machine 234-2 includes a software implementation of a machine (e.g., a computer) that executes programs like a physical machine. Virtual machine 234-2 may be either a system virtual machine or a process virtual machine, depending upon use and degree of correspondence to any real machine by virtual machine 234-2. A system virtual machine may provide a complete system platform that supports execution of a complete operating system ("OS"). A process virtual machine may execute a single program, and may support a single process. In some implementations, virtual machine 234-2 may execute on behalf of a user (e.g., a user of client device 210), and may manage infrastructure of cloud computing environment 232, such as data management, synchronization, or long-duration data transfers.

Virtualized storage 234-3 includes one or more storage systems and/or one or more devices that use virtualization techniques within the storage systems or devices of computing resource 234. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 234-4 provides hardware virtualization techniques that allow multiple operating systems (e.g., "guest operating systems") to execute concurrently on a host computer, such as computing resource 234. Hypervisor 234-4 may present a virtual operating platform to the guest operating systems, and may manage the execution of the guest operating systems. Multiple instances of a variety of operating systems may share virtualized hardware resources.

Network 240 includes one or more wired and/or wireless networks. For example, network 240 may include a cellular network (e.g., a long-term evolution (LTE) network, a code division multiple access (CDMA) network, a 3G network, a 4G network, a 5G network, or another type of cellular network), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, and/or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
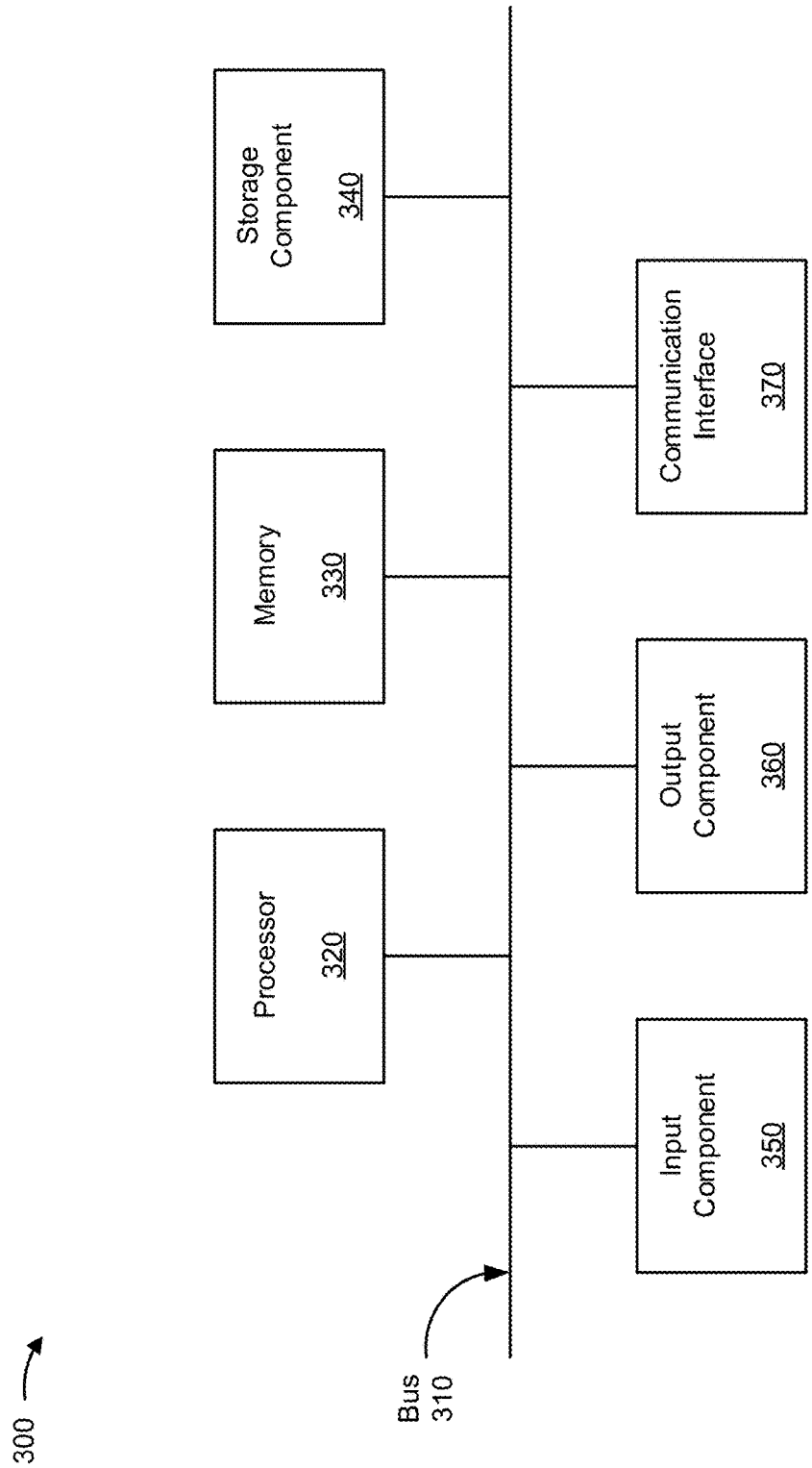
FIG. 3 is a diagram of example components of one or more devices of FIG. 2.

FIG. 3 is a diagram of example components of a device 300. Device 300 may correspond to client device 210, external information source 220, and/or recommendation platform 230. In some implementations, client device 210, external information source 220, and/or recommendation platform 230 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 includes a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operations and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes in response to processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
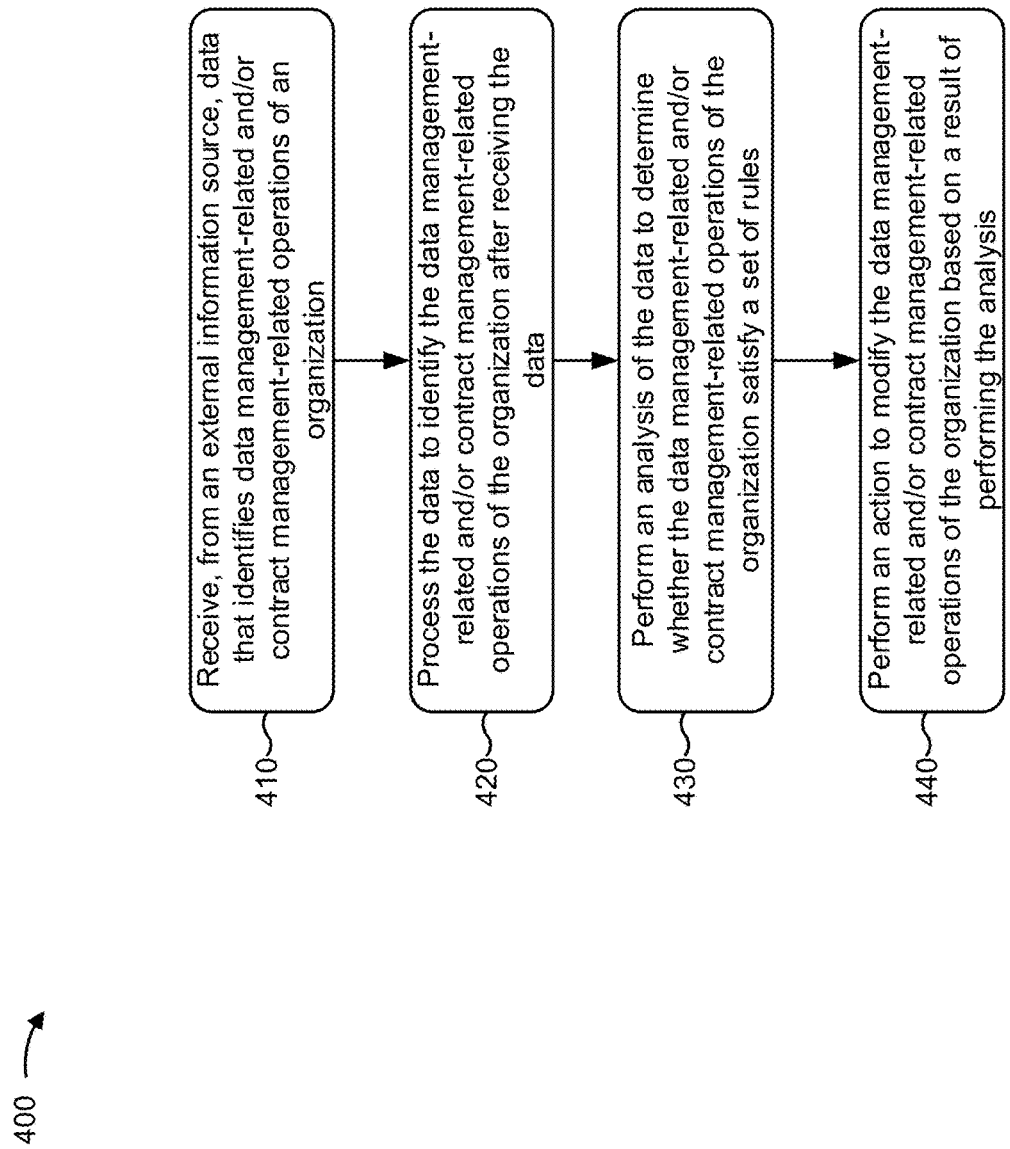
FIG. 4 is a flow chart of an example process for analyzing data management-related and/or contract management-related operations of an organization.

FIG. 4 is a flow chart of an example process 400 for analyzing data management-related and/or contract management-related operations of an organization. In some implementations, one or more process blocks of FIG. 4 may be performed by recommendation platform 230. In some implementations, one or more process blocks of FIG. 4 may be performed by another device or a group of devices separate from or including recommendation platform 230, such as client device 210 and external information source 220.

As shown in FIG. 4, process 400 may include receiving, from an external information source, data that identifies data management-related and/or contract management-related operations of an organization (block 410). For example, recommendation platform 230 may receive, from external information source 220, data that identifies data management-related and/or contract management-related operations of an organization. In some implementations, recommendation platform 230 may receive the data periodically, according to a schedule, based on input from a user of client device 210, based on requesting the information, and/or the like.

In some implementations, recommendation platform 230 may receive the data from external information source 220. In some implementations, recommendation platform 230 may receive the data from a system. For example, in a healthcare context, recommendation platform 230 may receive the data from a system associated with a healthcare plan and/or a system associated with a healthcare provider.

In some implementations, the operations may include permissions for manipulating the data stored in a system, how the data stored in a system can be manipulated, at what points (e.g., during a process that uses the data stored in a system) the data can be manipulated, the types of data being stored, a manner in which two organizations contract for services, whether and/or the manner in which an organization verifies an accuracy and/or consistency of data stored in a system (e.g., data quality control procedures of an organization), and/or the like.

In some implementations, for example, the operations may include network development operations (e.g., types of hardware resources used to store data, controls/validation related to electronic signature data for a contract, whether the organization gathers metrics related to stored data, such as for analytics, etc.). Additionally, or alternatively, and as another example, the operations may include credentialing and/or re-credentialing operations (e.g., automated credentialing technology, mechanisms for outsourcing credentialing functions, consolidation of credentialing resources, two-way integration technology, etc.).

Additionally, or alternatively, and as another example, the operations may include operations for maintaining data (e.g., integration of multiple organization systems), resources for entering and/or validating data, whether business processes, data loading processes, etc. are automated, and/or the like. Additionally, or alternatively, and as another example, the operations may include operations for maintaining pricing (e.g., automation of linkage between contract and pricing systems, automation of processes to enforce business rules, implementation and/or consolidation of pricing and modeling systems, etc.). Additionally, or alternatively, and as another example, the operations may include operations relating to service providers (e.g., integration of maintenance requests among web, online, paper, and/or the like, systems for documenting and/or providing education information to customers, implementation of customer portals, online maintenance, etc.).

In some implementations, the data may include text (e.g., text from text files, word processing documents, spreadsheets, etc., such as may be associated with contracts, policy information, etc.), audio data, and/or video data. Additionally, or alternatively, the data may include metadata. In some implementations, recommendation platform 230 may receive the data in a file. For example, recommendation platform 230 may receive the data in a comma separated values (CSV) file, a spreadsheet file, a text file, a hypertext markup language (HTML) file, an extensible markup language (XML) file, and/or the like. In this way, recommendation platform 230 may receive various types of data and/or file types, thereby permitting recommendation platform 230 to dynamically receive data.

In some implementations, recommendation platform 230 may receive millions, billions, or trillions of data elements when receiving the data. In this way, recommendation platform 230 may receive a data set that cannot be received manually and/or processed objectively.

In some implementations, recommendation platform 230 may store the data. For example, recommendation platform 230 may store the data using memory resources of recommendation platform 230. In some implementations, when storing the data, recommendation platform 230 may aggregate and/or merge the data with other data, deduplicate the data, identify missing or corrupted data and obtain replacement data (e.g., using information related to the data, querying data from external information sources 220, cross-referencing the data to identify the missing and/or corrupted data, and/or the like). In some implementations, recommendation platform 230 may use a big data tool to aggregate and/or merge the data. In this way, recommendation platform 230 may prepare a data set for analysis that cannot be prepared manually. In addition, in this way, recommendation platform 230 may reduce errors associated with the data, thereby conserving processing resources of recommendation platform 230 that would otherwise be consumed due to analysis using error-containing data.

In this way, recommendation platform 230 may receive, from external information source 220, data that identifies data management-related operations of an organization.

As further shown in FIG. 4, process 400 may include processing the data to identify the data management-related and/or contract management-related operations of the organization after receiving the data (block 420). For example, recommendation platform 230 may process the data to identify the data management-related and/or contract management-related operations of the organization. In some implementations, recommendation platform 230 may process millions, billions, or trillions of data elements. In this way, recommendation platform 230 may process a data set that cannot be processed manually and/or objectively.

In some implementations, recommendation platform 230 may process the data using a technique. In some implementations, and for example, recommendation platform 230 may process the data using natural language processing to identify a term, a phrase (e.g., multiple terms), and/or the like that indicates the data management-related and/or contract management-related operations. In this way, recommendation platform 230 may automatically, quickly, and efficiently identify a term or a phrase that may indicate data management-related and/or contract management-related operations.

Additionally, or alternatively, and as another example, recommendation platform 230 may process the data using artificial intelligence to identify patterns in the data that indicate data management-related and/or contract management-related operations of the organization. For example, recommendation platform 230 may use artificial intelligence to identify a pattern or a trend in data formatting, such as a pattern of 10-digit telephone numbers rather than 7-digit telephone numbers (e.g., when analyzing operations related to storing information such as telephone numbers), systems in which particular types of data are stored, a type of data used to perform a particular process, and/or the like. In this way, recommendation platform 230 may automatically, quickly, and efficiently identify a trend or pattern that may indicate data management-related and/or contract management-related operations of an organization.

Additionally, or alternatively, and as another example, recommendation platform 230 may process the data using machine learning to identify data management-related and/or contract management-related operations, where recommendation platform 230 has been trained on data related to data management-related and/or contract management-related operations of other organizations. In this way, recommendation platform 230 may automatically, quickly, and efficiently determine data management-related and/or contract management-related operations using information related to operations of another organization.

Additionally, or alternatively, and as another example, recommendation platform 230 may process the data using computational linguistics, speech-to-text, computer speech recognition, automatic speech recognition, and/or the like to identify a term or a phrase in audio data that indicates data management-related and/or contract management-related operations of the organization. For example, recommendation platform 230 may identify a term or phrase in audio data from a customer service call, from an interview with an employee of an organization, and/or the like. In this way, recommendation platform 230 may process audio data and/or video data to permit identification of data management-related and/or contract management-related operations. In some implementations, recommendation platform 230 may process a file that includes the data or may process multiple files that include the data.

In some implementations, recommendation platform 230 may process the data using a technique to obtain information that identifies the operations of the organization, to apply a standard formatting to the data to permit recommendation platform 230 to analyze the data, to reduce or eliminate errors included in the data (e.g., thereby improving an analysis of the data), and/or the like. This conserves processing resources relative to another recommendation platform 230 that uses unprocessed data.

In this way, recommendation platform 230 may process data to identify data management-related and/or contract management-related operations of an organization.

As further shown in FIG. 4, process 400 may include performing an analysis of the data to determine whether the data management-related and/or contract management-related operations of the organization satisfy a set of rules (block 430). For example, recommendation platform 230 may perform an analysis of the data to determine whether the data management-related and/or contract management-related operations of the organization satisfy a set of rules. In some implementations, the set of rules may include a set of rules that identifies a manner in which an organization is to operate (e.g., rules defined by an organization, industry standard and/or benchmark rules, etc.).

In some implementations, recommendation platform 230 may obtain the set of rules from processing a document (e.g., using natural language processing), from processing an interview of an employee (e.g., where audio is converted to text using computational linguistics, speech-to-text, computer speech recognition, automatic speech recognition, etc.), performing machine learning on data from other organizations, such as to identify an industry standard for operating, and/or the like. Additionally, or alternatively, recommendation platform 230 may obtain the rules using an operating model. In some implementations, an operating model may include a model that identifies an area (e.g., a functional area and/or sub-area of a functional area of an organization that the organization uses to implement a data management-related process and/or operations).

In some implementations, the operating model may be based on analyses of other organizations. For example, the operating model may represent a benchmark structure and/or organizational structure of another organization (e.g., an organization identified as a high-performing organization or as having proper data management-related and/or contract management-related operations), an industry standard, and/or the like. In some implementations, recommendation platform 230 may use the operating model to identify a rule (e.g., related to data management-related and/or contract management-related operations, a functional area, or a sub-area), a threshold related to data, an industry standard, a metric related to a process and/or operations of an organization, and/or the like to apply to data related to a process and/or operations of an organization when analyzing the data.

In some implementations, recommendation platform 230 may map data to the organization operating model to identify the set of rules (e.g., map the data to a functional area and/or a sub-area of an organization operating model). In some implementations, for example, recommendation platform 230 may map the data using an identifier that identifies a particular functional area and/or sub-area with which the data is associated. Additionally, or alternatively, and as another example, recommendation platform 230 may map the data based on a functional area and/or sub-area of another organization with which data for similar operations is associated. This permits recommendation platform 230 to quickly identify a rule, a threshold, a metric, and/or the like by mapping data to an organization operating model.

In some implementations, recommendation platform 230 may analyze operations related to contracting to determine whether the operations related to contracting satisfy a set of rules. For example, recommendation platform 230 may analyze a manner in which an organization creates, manages, and negotiates a contract with another organization (e.g., via use and/or availability of stored contract templates, stored data related to negotiated terms, etc.).

In some implementations, and as a specific example, recommendation platform 230 may analyze a process that a healthcare plan uses to recruit healthcare providers for the healthcare plan. For example, recommendation platform 230 may analyze a manner in which the healthcare plan processes requests from healthcare providers to join the healthcare plan (e.g., analyze use of a standard application, an electronic application, etc.). Additionally, or alternatively, and as another example, recommendation platform 230 may analyze whether and/or the manner in which the healthcare plan performs analytics to assess healthcare provider metrics (e.g., to determine whether to contract with the healthcare provider, whether to renew a contract with a healthcare provider, etc.). Additionally, or alternatively, and as another example, recommendation platform 230 may analyze a manner in which the healthcare plan communicates with providers (e.g., by analyzing data related to a frequency and/or type of communications between a healthcare provider and a patient, between a healthcare provider and an employee, and/or the like).

In some implementations, and as another specific example, recommendation platform 230 may analyze operations related to creation and/or management of contract templates that a healthcare plan uses to contract with a healthcare provider. For example, recommendation platform 230 may analyze whether the organization uses a standard template, whether the organization uses multiple versions of the same template, whether the organization uses standard terms for contracts (e.g., the same payment term, the same duration, etc.), whether a contract template, or other information related to contracting, is stored in a central location, and/or the like.

In some implementations, recommendation platform 230 may analyze a process of the organization used to develop a contract template. For example, recommendation platform 230 may determine whether the process includes developing a base template that can be customized, whether modification rules have been established, and/or the like. In some implementations, recommendation platform 230 may analyze a process of the organization related to managing templates. For example, recommendation platform 230 may determine whether the process allows a change to be made to established templates, determine templates that may be impacted by a particular proposed change, whether validation and/or approval is needed for a change, and/or the like.

In some implementations, recommendation platform 230 may participate in the process by validating user credentials (e.g., a security token, a username and password combination, etc.) before permitting a change to a template, recording a change and providing a report of the change to a manager, and/or the like. In this way, recommendation platform 230 improves contract management-related operations of an organization, thereby reducing errors related to contracting, which conserves processing resources of devices used in a contracting process and/or improves an efficiency of a contracting process.

In some implementations, recommendation platform 230 may analyze a process of the organization related to creation of payment terms. For example, and in a healthcare context, recommendation platform 230 may determine whether the process includes validating contract, billing, and/or claims requirements associated with a healthcare provider, assigning a type and/or identifier to a healthcare provider for payment purposes, establishing modification rules to payment terms (e.g., when and/or an extent to which a healthcare provider is permitted to charge a value outside of a range of values), and/or the like. In some implementations, recommendation platform 230 may analyze a process of the organization related to managing terms and template associations. For example, recommendation platform 230 may determine whether the process includes establishing linking rules, establishing customization rules, and/or the like for template contracts.

In some implementations, recommendation platform 230 may analyze operations related to creation and/or maintenance of healthcare provider contracts (e.g., in a healthcare context). For example, recommendation platform 230 may analyze selection and/or modification of healthcare provider information, templates, and/or payment terms, identification and management of existing contracts, and/or the like. Continuing with the previous example, recommendation platform 230 may determine whether particular templates are used with a threshold frequency, an amount of customization the organization makes to a template (e.g., by performing a comparison of text of the template and text of a final contract and identifying a threshold quantity of words changed, a threshold quantity of edits, etc.).

In some implementations, and as an example in a healthcare context, recommendation platform 230 may analyze a process of a healthcare plan to select and/or update healthcare provider information. For example, recommendation platform 230 may determine whether the process includes conducting a healthcare provider search for information related to a healthcare provider (e.g., where the search is used to determine an error associated with the information stored by the organization or to analyze a metric to identify potential new healthcare providers to add to a healthcare plan), updating information related to an existing healthcare provider (e.g., when an error is identified), and/or the like.

In some implementations, recommendation platform 230 may analyze a process of the organization related to selecting a template and/or payment terms. For example, and in a healthcare context, recommendation platform 230 may determine whether the process includes selection of a template type, selection of a healthcare provider type, and/or identifier, merging language of the template with standard or negotiated payment terms, verifying modification requirements, and/or the like.

In some implementations, recommendation platform 230 may analyze a process of the organization related to modifying a template and/or payment terms. For example, recommendation platform 230 may determine whether the process includes selecting items for modification, gaining approval for modifications, and/or the like. In some implementations, recommendation platform 230 may analyze a process of the organization related to searching for an existing contract stored by the organization. For example, recommendation platform 230 may determine whether the process includes identifying and/or selecting an existing agreement (e.g., for viewing, for maintenance, or for use as a template).

In some implementations, and as an example in a healthcare context, recommendation platform 230 may analyze operations related to negotiation and/or approval of healthcare provider contracts. For example, recommendation platform 230 may analyze a financial impact of a healthcare provider contract (e.g., by using machine learning and/or artificial intelligence to analyze financial data of other healthcare provider contracts to predict a financial impact of a particular healthcare provider contract), submission of a healthcare provider contract to a healthcare provider (e.g., data that identifies whether a contract is submitted to a healthcare provider via mail, email, web portal, etc.), revisions to a healthcare provider contract (e.g., a quantity of edits made and/or words changed), addition of documents to a healthcare provider contract (e.g., a quantity and/or type of appendices or exhibits associated with the contract), and/or execution of a healthcare provider contract (e.g., a quantity of healthcare providers that have agreed to a proposed contract, whether a particular contract is in default, etc.), and/or the like.

In some implementations, recommendation platform 230 may analyze a process of the organization related to verifying additional documents related to a contract. For example, recommendation platform 230 may determine whether the process includes verification of adding a credentialing application, a W-9 form, a roster of physicians and/or locations of a healthcare provider, validating documents against a checklist (e.g., by using information identifying a type of the document), storing the documents in a manner such that the documents are associated with a contract, and/or the like.

In some implementations, recommendation platform 230 may analyze a process of the organization related to executing a contract. For example, recommendation platform 230 may determine whether the process includes attaining a signature from another organization, attaining an internal signature, attaching signed documents to the contract, storing the contract, and/or the like. In some implementations, and in a healthcare context, recommendation platform 230 may analyze a process of the organization related to submitting an executed contract for on-boarding of a healthcare provider to a healthcare plan. For example, recommendation platform 230 may determine whether the process includes validating that particular forms are completed, validating that the healthcare provider has submitted needed on-boarding documents to appropriate teams of a healthcare plan (e.g., a W-9 form, descriptions of services provided, etc.), and/or the like.

In some implementations, recommendation platform 230 may identify points during a process where data is input to a system, determine whether the same data can be input at multiple points in a process, into multiple systems, and/or the like. Additionally, or alternatively, recommendation platform 230 may analyze whether the organization is implementing controls related to data management. For example, recommendation platform 230 may analyze whether data can be manipulated without approval, whether the same data stored in different systems can be separately manipulated, whether data updates are pushed to other systems, and/or the like.

In some implementations, and as an example in a healthcare context, recommendation platform 230 may analyze data stored in a healthcare plan system and a healthcare provider system to determine whether the same data that is stored in both systems match (e.g., using analytics). For example, recommendation platform 230 may perform data reconciliation when the same data stored in both systems do not match (e.g., may copy data from one system to another system).

In some implementations, recommendation platform 230 may perform an audit of data stored by a system. In some implementations, and as an example in a healthcare context, recommendation platform 230 may identify contact information for a healthcare provider stored in a healthcare plan system. In this case, recommendation platform 230 may verify the contact information by attempting to contact the healthcare provider by sending a message to client device 210 associated with the healthcare provider using the contact information, calling a telephone of the healthcare provider using the contact information, processing data from a webpage associated with the healthcare provider, and/or the like.

Additionally, or alternatively, recommendation platform 230 may select particular data to audit prior to auditing the data (e.g., based on a threshold frequency of use of the data, whether the data can be manipulated at a threshold quantity of points in a process or by a threshold quantity of people, user input from client device 210, etc.). For example, with respect to data associated with a healthcare provider, recommendation platform 230 may select data associated with frequently used healthcare providers (e.g., healthcare providers that submit a threshold quantity of claims to a healthcare plan). In this way, recommendation platform 230 increases an efficiency of performing an audit of data. Additionally, or alternatively, recommendation platform 230 may update data when recommendation platform 230 fails to verify the data (e.g., when data in a first system fails to match data in a second system).

In some implementations, and in a healthcare context, recommendation platform 230 may perform an analysis of a claim that a healthcare provider has submitted to a healthcare plan. In some implementations, when performing an analysis of a claim, recommendation platform 230 may extract claim data, such as from a data warehouse (e.g., on a quarterly basis). In some implementations, recommendation platform 230 may select (e.g., based on the extracted claim data) top healthcare providers (e.g., by cost and/or by volume) to include in analytics, and/or may select healthcare providers associated with a particular region.

In some implementations, recommendation platform 230 may analyze a pending claim (e.g., associated with the selected healthcare providers). For example, recommendation platform 230 may analyze the claim with respect to terms of a contract with which the claim is associated, demographics of a healthcare provider and/or a patient associated with the claim, an amount of time a claim has been pending, a reason for the pendency (e.g., as indicated by an identifier), and/or the like. In some implementations, recommendation platform 230 may identify a discrepancy in the analyzed pending claim and may identify a data attribute causing the discrepancy. In some implementations, recommendation platform 230 may update information (e.g., based on identifying the discrepancy and/or the data attribute).

In this way, recommendation platform 230 may perform an analysis of data to determine whether data management-related and/or contract management-related operations of an organization satisfy a set of rules.

As further shown in FIG. 4, process 400 may include performing an action to modify the data management-related and/or contract management-related operations of the organization based on a result of performing the analysis (block 440). For example, recommendation platform 230 may perform an action to modify the data management-related and/or contract management-related operations of the organization based on a result of performing the analysis.

In some implementations, the action may improve, or positively impact a process and/or operations of an organization. In some implementations, an improvement or a positive impact may occur when an action causes a desired result or action to be achieved. Additionally, or alternatively, an improvement or a positive impact may occur when an action increases a likelihood that a desired result of an action will be achieved.

In some implementations, recommendation platform 230 may generate a recommendation. In some implementations, and for example, recommendation platform 230 may generate a recommendation to utilize a contract management system to store and/or administer contracts, rather than manually assembling the contracts, thereby reducing time needed to store and/or administer the contracts, improving accuracy of data related to the contracts, and/or the like.

Additionally, or alternatively, and as another example, recommendation platform 230 may generate a recommendation to identify and utilize a single system of record (instead of multiple systems) to maintain data, thereby reducing time needed to maintain the data, improving consistency of the data, and/or the like. Additionally, or alternatively, and as another example, recommendation platform 230 may generate a recommendation to automate a process (e.g., a data validation process), a process for loading data, etc., thereby reducing time needed to perform the process, improving accuracy of the process, and/or the like.

In some implementations, recommendation platform 230 may send a message (e.g., an email or short message service (SMS) message) to client device 210. For example, the message may include information related to the analysis. As another example, the message may include a set of instructions to implement a recommendation. Continuing with the previous example, the message may include a set of instructions to implement a recommendation (e.g., to implement data reconciliation, to prevent data manipulation at multiple points in a process, etc.). In some implementations, recommendation platform 230 may schedule a meeting (e.g., to discuss the analysis). For example, recommendation platform 230 may schedule the meeting using electronic calendars.

In some implementations, recommendation platform 230 may provide information for an analysis to another recommendation platform 230 (e.g., for use in machine learning). In this way, recommendation platform 230 improves future analyses of the other recommendation platform 230. In some implementations, recommendation platform 230 may generate a report. For example, recommendation platform 230 may generate a report that identifies data management-related and/or contract management-related operations that fail to satisfy a rule. In some implementations, recommendation platform 230 may perform a test of data management-related and/or contract management-related operations (e.g., after a change to the data management-related and/or contract management-related operations). For example, recommendation platform 230 may modify data stored in a first system and determine whether the modified data is pushed to other systems to ensure consistency of data across systems. In some implementations, recommendation platform 230 may generate a report that identifies a result of the test.

In this way, recommendation platform 230 may perform an action to modify data management-related and/or contract management-related operations of an organization based on a result of performing an analysis.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5A:
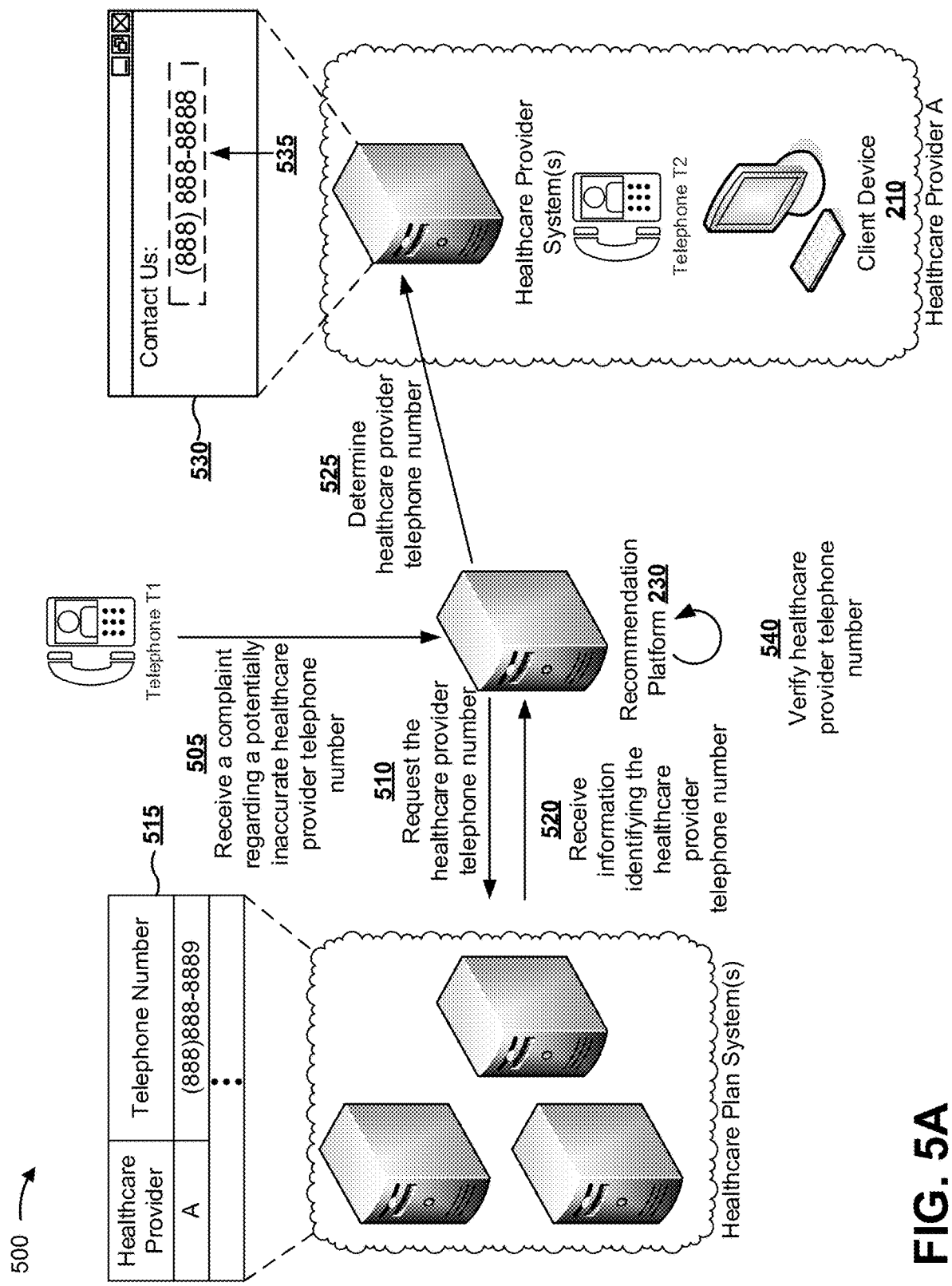
FIGS. 5A-5C are diagrams of an example implementation relating to the example process shown in FIG. 4.
Figure 5B:
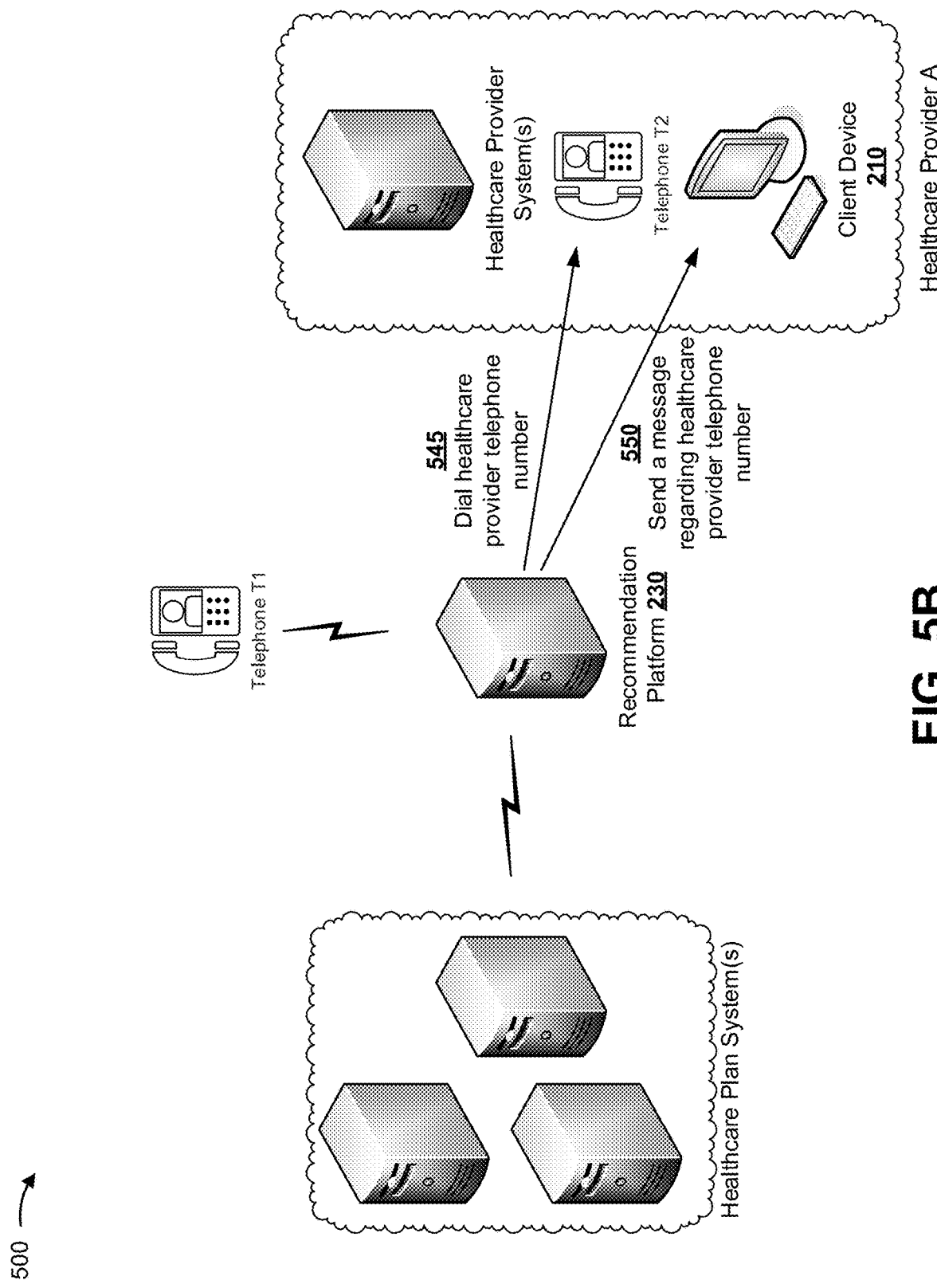
Figure 5C:
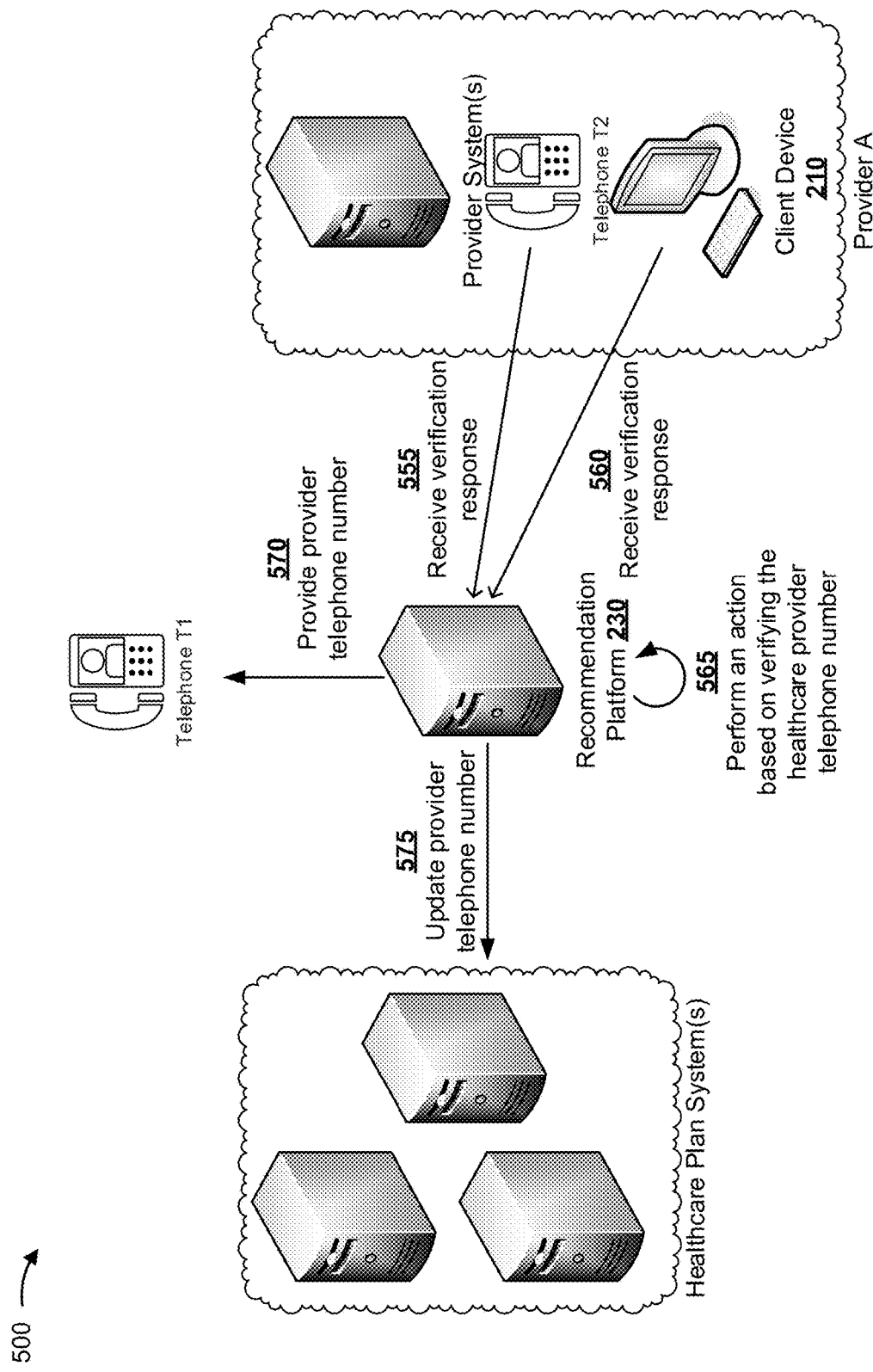

FIGS. 5A-5C are diagrams of an example implementation 500 relating to example process 400 shown in FIG. 4. FIGS. 5A-5C show an example of analyzing data management-related operations of an organization (e.g., a healthcare plan and/or a healthcare provider).

As shown in FIGS. 5A-5C, example implementation 500 may include recommendation platform 230, healthcare plan system(s) and provider system(s). FIGS. 5A-5C show an example of auditing healthcare provider data. In this case, recommendation platform 230 may receive a complaint that a telephone number for a particular healthcare provider (as obtained via the healthcare plan system(s)) was incorrect, and then audit the information in the healthcare plan system(s) by scanning a website associated with the healthcare provider and contacting the healthcare provider.

As shown in FIG. 5A, and as shown by reference number 505, recommendation platform 230 may receive a complaint from telephone T1 regarding a potentially inaccurate healthcare provider telephone number (e.g., for healthcare provider A). As shown by reference number 510, recommendation platform 230 may provide, to the healthcare plan system(s), a request for the healthcare provider telephone number stored by the healthcare plan system(s). As shown by reference number 515, the healthcare plan system(s) may access a record (e.g., in a database) to identify the potentially inaccurate telephone number. As shown by reference number 520, recommendation platform 230 may receive information identifying the healthcare provider telephone number from the healthcare plan system(s).

As shown by reference number 525, recommendation platform 230 may contact the healthcare provider system(s) (e.g., of healthcare provider A) to determine the correct telephone number. As shown by reference number 530, recommendation platform 230 may parse text of a webpage, or other record, associated with healthcare provider A to identify the correct telephone number. For example, as shown by reference number 535, recommendation platform 230 may use image processing, natural language processing, etc. to identify a telephone number on a "Contact Us" webpage associated with healthcare provider A.

As shown by reference number 540, recommendation platform 230 may verify the healthcare provider telephone number, as described in more detail below. For example, recommendation platform 230 may verify the healthcare provider telephone number prior to updating the telephone number stored in the healthcare plan system(s), to determine whether the complaint was accurate, to determine whether the telephone number stored in the healthcare provider system(s) is accurate, and/or the like. In this way, recommendation platform 230 improves an audit of data of an organization, thereby conserving processing resources related to updating data in a system.

As shown in FIG. 5B, and as shown by reference number 545, recommendation platform 230 may dial the healthcare provider telephone number of telephone T2 obtained from the healthcare provider system(s). For example, recommendation platform 230 may dial the telephone number to determine whether the telephone number is the correct number for healthcare provider A. As shown by reference number 550, recommendation platform 230 may send, to client device 210 associated with healthcare provider A, a message regarding the healthcare provider telephone number. For example, recommendation platform 230 may send a message requesting confirmation of the telephone number.

As shown in FIG. 5C, and as shown by reference number 555, recommendation platform 230 may receive a verification response from telephone T2. For example, recommendation platform 230 may receive audio confirmation of the telephone number, confirmation via a touchpad of telephone T2, and/or the like. As shown by reference number 560, recommendation platform 230 may receive a verification response from client device 210. For example, recommendation platform 230 may receive a message from client device 210 indicating whether the telephone number of healthcare provider A is correct.

As shown by reference number 565, recommendation platform 230 may perform an action based on verifying the healthcare provider telephone number. In some implementations, as shown by reference number 570, recommendation platform 230 may provide the telephone number to telephone T1. Additionally, or alternatively, as shown by reference number 575, recommendation platform 230 may provide an update of the healthcare provider telephone number to the healthcare plan system(s). In this way, recommendation platform 230 may perform an audit of data related to a healthcare provider and may update data when an error is identified.

As indicated above, FIGS. 5A-5C are provided merely as an example. Other examples are possible and may differ from what was described with regard to FIGS. 5A-5C.

Figure 6:
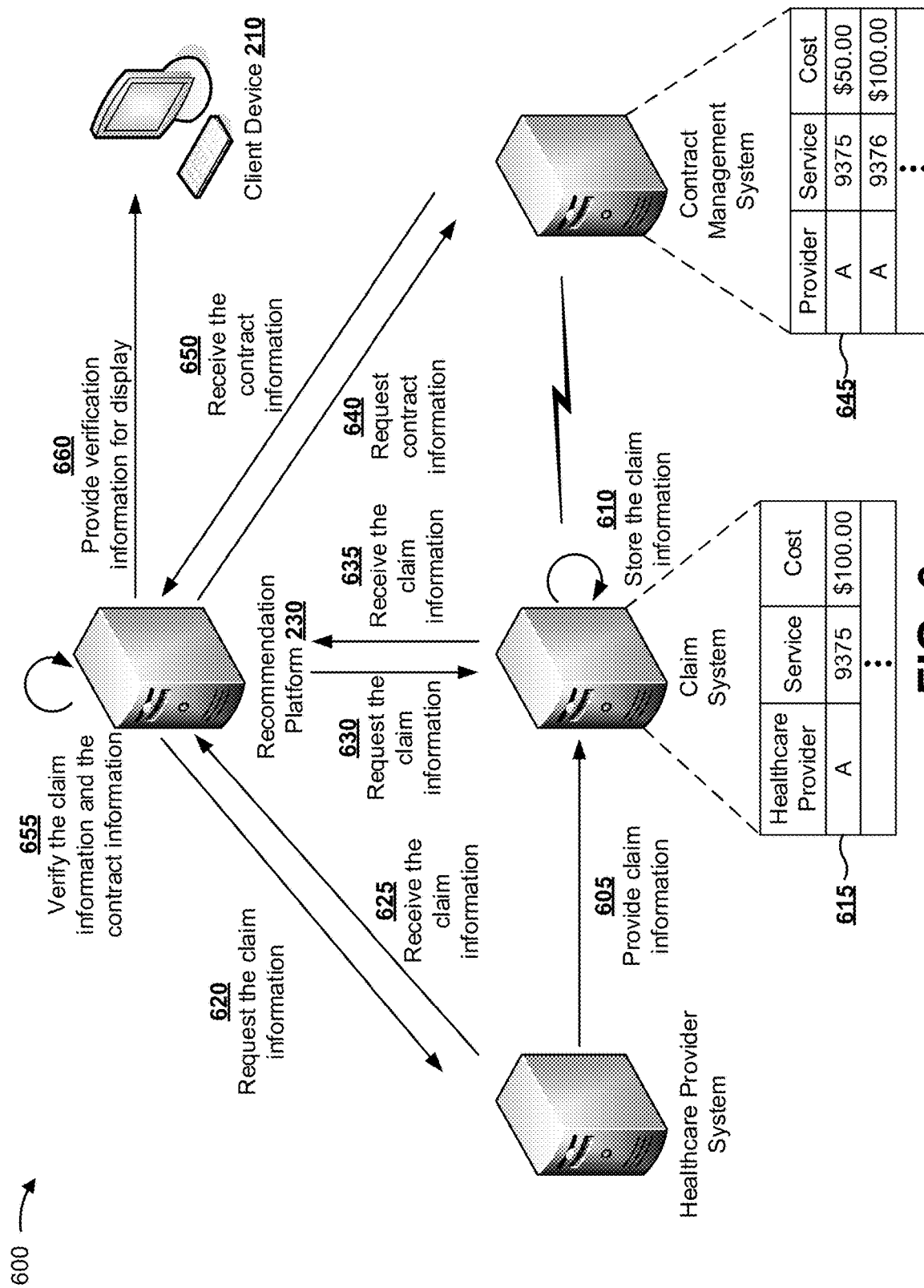
FIG. 6 is a diagram of an example implementation relating to the example process shown in FIG. 4.

FIG. 6 is a diagram of an example implementation 600 relating to example process 400 shown in FIG. 4. FIG. 6 shows an example of analyzing data management-related and/or contract management-related operations of an organization.

As shown in FIG. 6, example implementation 600 may include client device 210, recommendation platform 230, a healthcare provider system, a claim system, and a contract management system. FIG. 6 shows an example of recommendation platform 230 auditing a claim from a healthcare provider. In this example, recommendation platform 230 may compare claim information in the healthcare provider system (e.g., associated with a claim sent to a claim system), claim information stored by the claim system associated with a healthcare plan (e.g., associated with a claim received by the claim system), and information in the contract management system (e.g., identifying types of claims and amounts that a particular healthcare provider is permitted to submit). In this case, recommendation platform 230 may perform the audit to determine whether an error occurred when providing and/or receiving the claim information, and to determine whether the healthcare provider submitted a proper claim (e.g., for a permitted service and/or amount).

As shown in FIG. 6, and by reference number 605, the healthcare provider system may provide claim information to the claim system (e.g., claim information associated with a claim submitted to a healthcare plan). As shown by reference number 610, the claim system may store the claim information. For example, as shown by reference number 615, the claim system may store a record for the claim information (e.g., information identifying the claim as being associated with healthcare provider A, a service identifier identifying a service that healthcare provider A provided, and information identifying a cost of the service that healthcare provider A provided).

As shown by reference number 620, recommendation platform 230 may request the claim information from the healthcare provider system (e.g., claim information submitted to a healthcare plan). As shown by reference number 625, recommendation platform 230 may receive the requested claim information from the healthcare provider system. Recommendation platform 230 may request the claim information to perform an analysis of the claim information, as described below.

As shown by reference number 630, recommendation platform 230 may request the claim information from the claim system (e.g., claim information received and/or stored by a healthcare plan). As shown by reference number 635, recommendation platform 230 may receive the claim information from the claim system. Recommendation platform 230 may request the claim information from the claim system, despite also requesting the claim information from the healthcare provider system, to permit a comparison of the claim information that the healthcare provider system and the claim system have stored.

As shown by reference number 640, recommendation platform 230 may request contract information from the contract management system (e.g., a contract associated with a claim being analyzed). As shown by reference number 645, the contract management system may perform a lookup of the requested contract information. For example, the contract management system may perform a lookup of a service that healthcare provider A provides using a service identifier and/or a cost which healthcare provider A is permitted to bill a healthcare plan for providing the service. As shown by reference number 650, recommendation platform 230 may receive the requested contract information from the contract management system. Recommendation platform 230 may request the contract information from the contract management system to permit recommendation platform 230 to determine whether claim information satisfies contract information, as described below.

As shown by reference number 655, recommendation platform 230 may verify the claim information and the contract information. For example, recommendation platform 230 may determine whether the claim information for a claim satisfies contract information (e.g., determine whether a claim that a healthcare provider submits to a healthcare plan satisfies a contract between the healthcare provider and the healthcare plan). In this case, recommendation platform 230 may identify an error associated with the claim information (e.g., that a cost of a service provided by healthcare provider A exceeds the cost permitted by a contract between the healthcare provider and a healthcare plan). As shown by reference number 660, recommendation platform 230 may provide verification information indicating a result of the analysis to client device 210 (e.g., for display).

As indicated above, FIG. 6 is provided merely as an example. Other examples are possible and may differ from what was described with regard to FIG. 6.

Figure 7A:
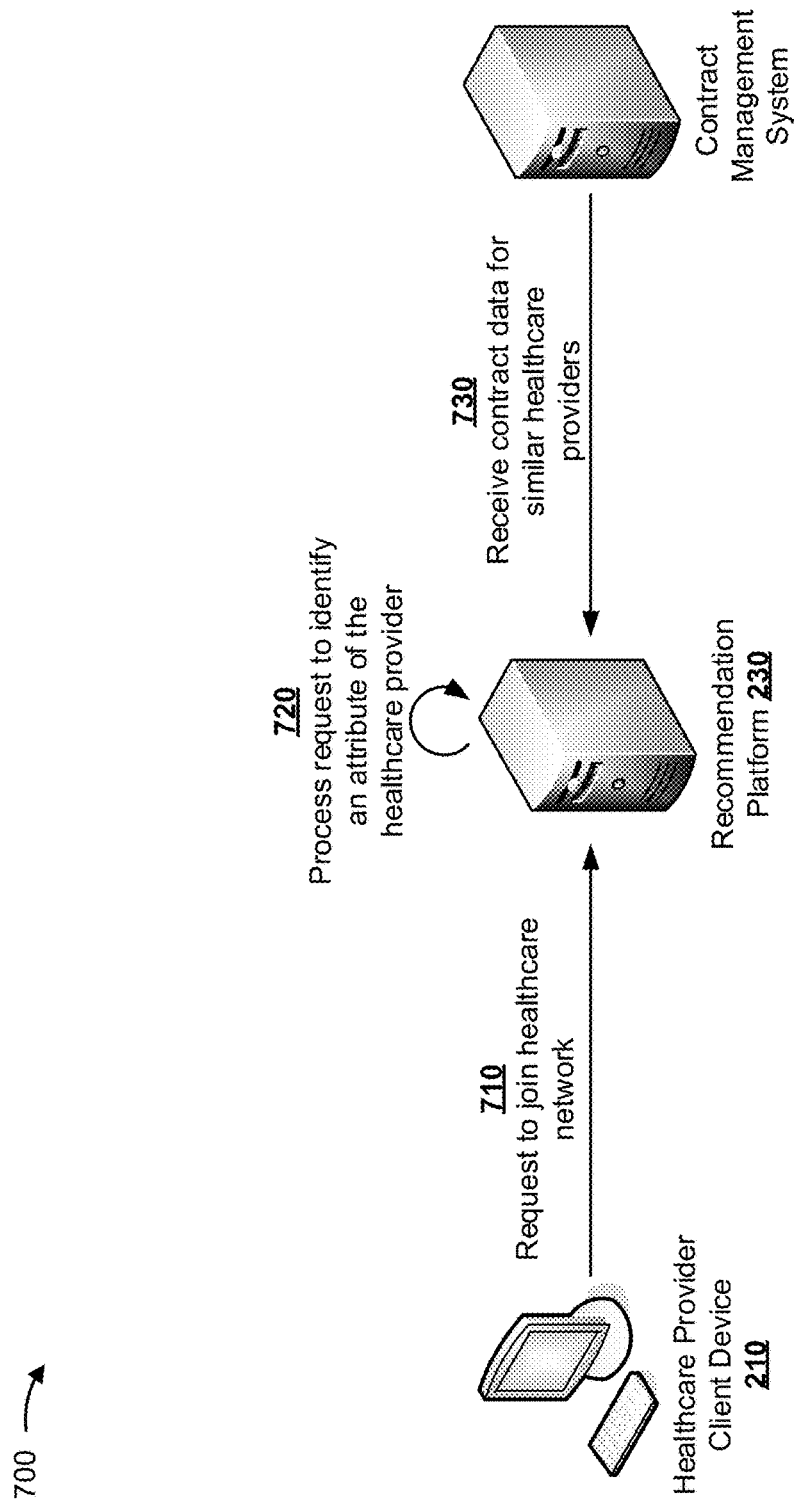
FIGS. 7A and 7B are diagrams of an example implementation relating to the example process shown in FIG. 4.
Figure 7B:
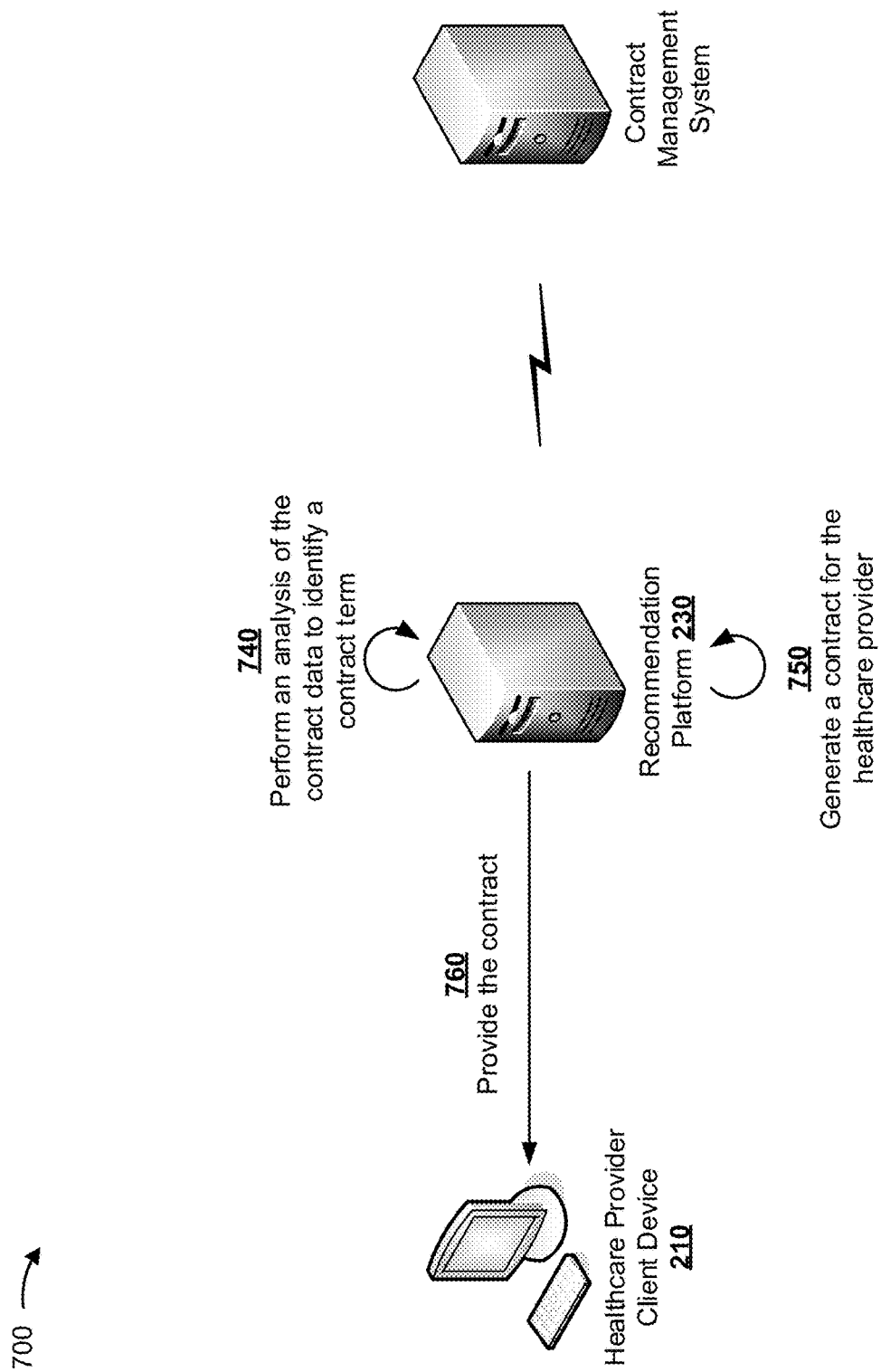

FIGS. 7A and 7B are diagrams of an example implementation 700 relating to example process 400 shown in FIG. 4. FIGS. 7A and 7B show an example of analyzing data management-related and/or contract management-related operations of an organization.

As shown in FIGS. 7A and 7B, example implementation 700 may include client device 210 associated with a healthcare provider (e.g., a healthcare provider client device 210), recommendation platform 230, and a contract management system associated with a healthcare network. FIGS. 7A and 7B show an example of recommendation platform 230 improving a contracting process between a healthcare plan and a healthcare provider.

As shown in FIG. 7A, and as shown by reference number 710, recommendation platform 230 may receive, from healthcare provider client device 210, a request to join a healthcare network. As shown by reference number 720, recommendation platform 230 may process the request to identify an attribute of the healthcare provider. For example, an attribute may include a type of service provided by the healthcare provider, a geographic location of the healthcare provider, years of experience of the healthcare provider, and/or the like. As shown by reference number 730, recommendation platform 230 may receive, from the contract management system, contract data for similar healthcare providers. For example, a similar healthcare provider may include a healthcare provider with a same or a similar attribute as the healthcare provider making the request (e.g., in the same or an adjacent geographic region, that provide the same or similar types of services, etc.).

As shown in FIG. 7B, and as shown by reference number 740, recommendation platform 230 may perform an analysis of the contract data to identify a contract term. For example, recommendation platform 230 may analyze historical contract terms for other healthcare providers, whether the historical contract terms vary from provider to provider, an average and/or range of values for services provided by other providers, and/or the like. As shown by reference number 750, recommendation platform 230 may generate a contract for the healthcare provider. For example, recommendation platform 230 may generate a contract term for the healthcare provider based on analyzing the contract data for the similar healthcare providers. As a particular example, recommendation platform 230 may generate a value for services that is an average of the other similar healthcare providers, a value for services that is within a range of the other healthcare providers, and/or the like. Continuing with the previous examples, recommendation platform 230 include a generated contract term in a template contract for the healthcare provider. As shown by reference number 760, recommendation platform 230 may provide the contract to the healthcare provider client device 210 (e.g., for execution by the healthcare provider).

As indicated above, FIGS. 7A and 7B are provided merely as an example. Other examples are possible and may differ from what was described with regard to FIGS. 7A and 7B.

Figure 8B:
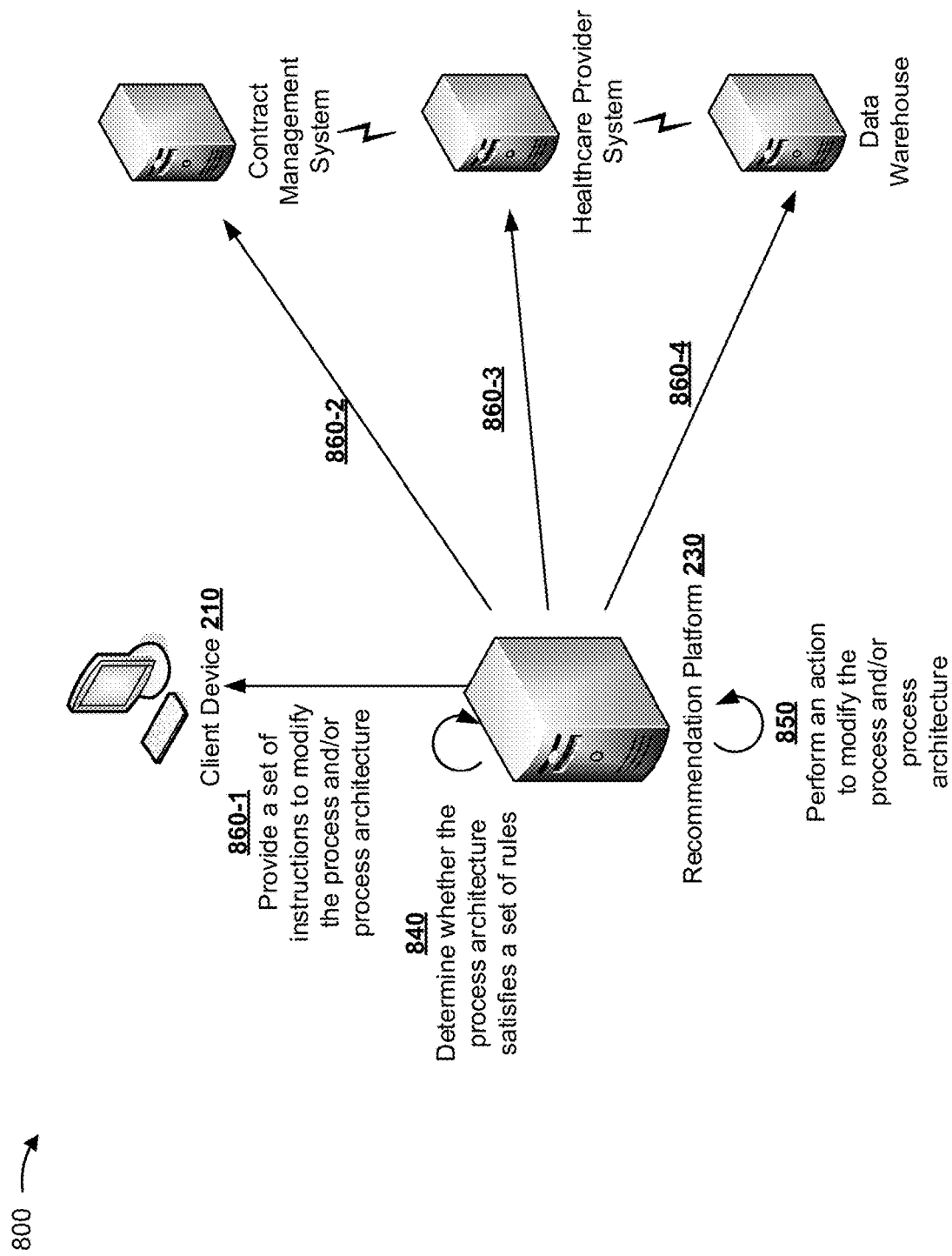

FIGS. 8A and 8B are diagrams of an example implementation 800 relating to example process 400 shown in FIG. 4. FIGS. 8A and 8B show an example of analyzing data management-related and/or contract management-related operations of an organization.

FIGS. 8A and 8B show recommendation platform 230 analyzing a process architecture for a process to determine whether data controls related to the process satisfy a set of rules. As shown in FIGS. 8A and 8B, example implementation 800 may include recommendation platform 230. In addition, as shown in FIG. 8B, example implementation 800 may include client device 210, a contract management system, a healthcare provider system, and a data warehouse.

As shown in FIG. 8A, and as shown by reference number 810, recommendation platform 230 may receive data that identifies a process architecture for a process. For example, the process architecture may include use of client devices 210-1 through 210-3, a contract management system, a healthcare provider system, and a data warehouse. As shown by reference number 820, recommendation platform 230 may process the data to identify the process architecture. For example, the process architecture may identify systems that implement a process, where data is input into the systems and/or manipulated during the process, and/or the like. As shown by reference numbers 830-1 through 830-3, recommendation platform 230 may determine that data may be input and/or manipulated at different points during the process based on identifying the process architecture.

As shown in FIG. 8B, and as shown by reference number 840, recommendation platform 230 may determine whether the process architecture satisfies a set of rules. For example, recommendation platform 230 may determine that the set of rules is not satisfied by determining that particular data can be input at multiple points during the process, that the same data stored in different systems can be manipulated separately without reconciliation, and/or the like. As shown by reference number 850, recommendation platform 230 may perform an action (e.g., provide a set of instructions) to modify the process and/or process architecture (e.g., to fix the failure to satisfy the set of rules).

As an example, recommendation platform 230 may determine that a rule requiring a single point of data entry is not satisfied when both the contract management system and the healthcare provider system allow data to be entered via different client devices 210, and may generate a report that includes an indication that the rule is not satisfied and identifies the process points that allow multiple points of data entry. As another example, recommendation platform 230 may determine that a rule requiring a single source of record is not satisfied when the same data stored in the healthcare provider system and the data warehouse can be separately manipulated without reconciliation of the same data between the healthcare provider system and the data warehouse, and may generate a recommendation to add a reconciliation function to the process.

As shown by reference numbers 860-1 through 860-4, recommendation platform 230 may provide a set of instructions to modify the process and/or process architecture, so that the process and/or process architecture satisfy a set of rules. For example, recommendation platform 230 may modify settings of client device 210 and/or a system to prevent data manipulation at multiple points in a process or in different systems. This improves data management-related operations and conserves processing resources that would be consumed due to data management-related and/or contract management-related operations failing to satisfy a set of rules.

As indicated above, FIGS. 8A and 8B are provided merely as an example. Other examples are possible and may differ from what was described with regard to FIGS. 8A and 8B. In addition, although example implementations 500 through 800 were described as separate examples, example implementations 500 through 800 can occur concurrently.

Some implementations, described herein, provide a recommendation platform that is capable of processing data to determine a manner in which an organization operates, particularly with respect to data management-related and/or contract management-related operations, determining whether the operations of the organization satisfy a set of rules, and/or performing an action to modify the operations of the organization to improve the operations. In this way, some implementations described herein increase an efficiency of the operations, thereby conserving processing resources of a device used to implement the operations. In addition, some implementations described herein reduce errors related to the operations, thereby conserving processing resources, of a device used to implement the operations, that would otherwise be consumed due to error-prone operations.

Although implementations are described herein in with respect to healthcare organizations, the implementations apply equally to other types of organizations. Further, although implementations are described herein with respect to data management-related operations and/or contract management-related operations, the implementations apply equally to other types of operations, such as supply chain management operations, manufacturing operations, retail operations, and/or the like.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, and/or a combination of hardware and software.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A device, comprising:
a memory; and
one or more processors to:
receive first data that identifies operations of a plurality of systems,
the first data being received from an external information source, and
the operations of the plurality of systems including:
a first operation integrating the plurality of systems, and
a second operation including:
permissions for manipulating second data stored in the plurality of systems, and
points during a particular process at which the second data can be manipulated;
process the first data, using one or more of artificial intelligence or machine learning, to identify the operations of the plurality of systems;
select particular data, from the second data, based on at least one of:
determining that the particular data can be manipulated at a threshold quantity of points during the particular process, or
determining that the particular data can be manipulated by a threshold quantity of people;
perform an analysis of the particular data to determine that the operations of the plurality of systems satisfy a set of rules,
the set of rules indicating a manner in which the plurality of systems are to operate, and
the analysis including an audit of the particular data;
perform, based on a result of the analysis, a plurality of actions reducing errors related to the operations of the plurality of systems,
the plurality of actions including:
a modification of the operations of the plurality of systems to create:
a modified first operation integrating the plurality of systems, and
a modified second operation including modified permissions for manipulating the second data, and
a modification of settings that prevent data manipulation at one or more of the points during the particular process; and
perform a test of the modified first operation and the modified second operation,
the test including:
a modification of a portion of the second data, stored in a first system of the plurality of systems, to create modified second data, and
a determination that the modified second data is transmitted from the first system to a second system, of the plurality of systems, ensuring consistency of the modified second data between the first system and the second system.

2. The device of claim 1, where the one or more processors are further to:
identify the set of rules using an operating model,
the operating model being based on operations of another plurality of systems; and
where the one or more processors, when performing the analysis, are to:
perform the analysis based on identifying the set of rules using the operating model.

3. The device of claim 2, where the one or more processors are further to:
map the first data to the operating model to permit identification of the set of rules; and
where the one or more processors, when identifying the set of rules, are to:
identify the set of rules based on mapping the first data to the operating model.

4. The device of claim 1, where the one or more processors are further to:
process third data that identifies other operations of another plurality of systems prior to performing the analysis; and
identify a trend related to the other operations of the other plurality of systems,
information identifying the trend to be used to analyze the operations of the plurality of systems; and
where the one or more processors, when performing the analysis, are to:
perform the analysis using the information identifying the trend.

5. The device of claim 1, where the analysis is a first analysis;
where the one or more processors are further to:
perform a second analysis using third data stored in the plurality of systems,
the plurality of system being associated with multiple organizations; and
where the one or more processors, when performing the plurality of actions, are further to:
perform an action to modify the third data stored in the plurality of systems.

6. The device of claim 1, where the plurality of actions further include:
a modification of the settings to prevent data manipulation at a plurality of points in different systems.

7. The device of claim 1, where the set of rules include a rule requiring a single point of data entry; and
where the modified second operation includes modified permissions such that the second data can only be manipulated at a single point during the particular process.

8. A method, comprising:
receiving, by a device, first data that identifies operations of a plurality of systems,
the first data being received from an external information source, and
the operations of the plurality of systems including:
a first operation integrating the plurality of systems, and
a second operation including:
permissions for manipulating second data stored in the plurality of systems, and
points during a particular process at which the second data can be manipulated;
processing, by the device and using one or more of artificial intelligence or machine learning, the first data to identify the operations of the plurality of systems;
selecting, by the device, particular data, from the second data, based on at least one of:
determining that the particular data can be manipulated at a threshold quantity of points during the particular process, or
determining that the particular data can be manipulated by a threshold quantity of people;

performing, by the device, an analysis of the particular data to determine that the operations of the plurality of systems satisfy a set of rules,
    the set of rules indicating a manner in which the plurality of systems are to operate, and
    the analysis including an audit of the particular data;
performing, by the device based on a result of the analysis, a plurality of actions reducing errors related to the operations of the plurality of systems,
    the plurality of actions including:
        modifying the operations of the plurality of systems to create:
            a modified first operation integrating the plurality of systems, and
            a modified second operation including modified permissions for manipulating the second data, and
        modifying settings that prevent data manipulation at one or more of the points during the particular process; and
performing, by the device, a test of the modified first operation and the modified second operation,
    the test including:
        modifying a portion of the second data, stored in a first system of the plurality of systems, to create modified second data, and
        determining that the modified second data is transmitted from the first system to a second system, of the plurality of systems, ensuring consistency of the modified second data between the first system and the second system.

9. The method of claim 8, further comprising:
identifying the set of rules using an operating model,
    the operating model being based on operations of another plurality of systems; and
where performing the analysis comprises:
    performing the analysis based on identifying the set of rules using the operating model.

10. The method of claim 9, further comprising:
mapping the first data to the operating model to permit identification of the set of rules; and
where identifying the set of rules comprises:
    identifying the set of rules based on mapping the first data to the operating model.

11. The method of claim 8, further comprising:
processing third data that identifies other operations of another plurality of systems prior to performing the analysis;
identifying a trend related to the other operations of the other plurality of systems,
    information identifying the trend to be used to analyze the operations of the plurality of systems; and
where performing the analysis comprises:
    performing the analysis using the information identifying the trend.

12. The method of claim 8, where the analysis is a first analysis;
where the method further comprises:
    performing a second analysis using third data stored in the plurality of systems,
        the plurality of systems being associated with multiple organizations; and
    where performing the plurality of actions further comprises:
        performing an action to modify the third data stored in the plurality of systems.

13. The method of claim 8, where the plurality of actions further include:
    modifying the settings to prevent data manipulation at a plurality of points in different systems.

14. The method of claim 8, where the set of rules include a rule requiring a single point of data entry; and
where the modified second operation includes modified permissions such that the second data can only be manipulated at a single point during the particular process.

15. A non-transitory computer-readable medium storing instructions, the instructions comprising:
one or more instructions that, when executed by one or more processors, cause the one or more processors to:
    receive first data that identifies operations of a plurality of systems,
        the first data being received from an external information source, and
        the operations of the plurality of systems including:
            a first operation integrating the plurality of systems, and
            a second operation including:
                permissions for manipulating second data stored in the plurality of systems, and
                points during a particular process at which the second data can be manipulated;
    process the first data, using one or more of artificial intelligence or machine learning, to identify the operations of the plurality of systems;
    select particular data, from the second data, based on at least one of:
        determining that the particular data can be manipulated at a threshold quantity of points during the particular process, or
        determining that the particular data can be manipulated by a threshold quantity of people;
    perform an analysis of the particular data to determine that the operations of the plurality of systems satisfy a set of rules,
        the set of rules indicating a manner in which the plurality of systems are to operate, and
        the analysis including an audit of the particular data;
    perform, based on a result of the analysis, plurality of actions reducing errors related to the operations of the plurality of systems,
        the plurality of actions including:
            a modification of the operations of the plurality of systems to create:
                a modified first operation integrating the plurality of systems, and
                a modified second operation including modified permissions for manipulating the second data, and
            a modification of settings that prevent data manipulation at one or more of the points during the particular process; and
    perform a test of the modified first operation and the modified second operation,
        the test including:
            a modification of a portion of the second data, stored in a first system of the plurality of systems, to create modified second data, and
            a determination that the modified second data is transmitted from the first system to a second system, of the plurality of systems, ensuring consistency of the modified second data between the first system and the second system.

16. The non-transitory computer-readable medium of claim 15, where the one or more instructions, when executed by the one or more processors, further cause the one or more processors to:
    identify the set of rules using an operating model,
        the operating model being based on operations of another plurality of systems; and
    where the one or more instructions, that cause the one or more processors to perform the analysis, cause the one or more processors to:
        perform the analysis based on identifying the set of rules using the operating model.

17. The non-transitory computer-readable medium of claim 16, where the one or more instructions, when executed by the one or more processors, further cause the one or more processors to:
    map the first data to the operating model to permit identification of the set of rules; and
    where the one or more instructions, that cause the one or more processors to identify the set of rules, cause the one or more processors to:
        identify the set of rules based on mapping the first data to the operating model.

18. The non-transitory computer-readable medium of claim 15, where the one or more instructions, when executed by the one or more processors, further cause the one or more processors to:
    process third data that identifies other operations of another plurality of systems prior to performing the analysis;
    identify a trend related to the other operations of the other plurality of systems,
        information identifying the trend to be used to analyze the operations of the plurality of systems; and
    where the one or more instructions, that cause the one or more processors to perform the analysis, cause the one or more processors to:
        perform the analysis using the information identifying the trend.

19. The non-transitory computer-readable medium of claim 15, where the analysis is a first analysis;
    where the one or more instructions, when executed by the one or more processors, further cause the one or more processor to:
        perform a second analysis using third data stored in the plurality of systems,
            the plurality of systems being associated with multiple organizations; and
        where the one or more instructions, that cause the one or more processors to perform the plurality of actions, further cause the one or more processors to:
            perform an action to modify the third data stored in the plurality of systems.

20. The non-transitory computer-readable medium of claim 15, where the plurality of actions further include:
    a modification of the settings to prevent data manipulation at a plurality of points in different systems.

* * * * *